United States Patent [19]

Cohen

[11] Patent Number: 5,520,176
[45] Date of Patent: May 28, 1996

[54] ITERATIVE SLEEP EVALUATION

[75] Inventor: Daniel E. Cohen, Eden Prairie, Minn.

[73] Assignee: Aequitron Medical, Inc., Plymouth, Minn.

[21] Appl. No.: 81,586

[22] Filed: Jun. 23, 1993

[51] Int. Cl.⁶ .................................................. A61B 5/04
[52] U.S. Cl. ..................... 128/630; 128/671; 128/731; 128/670
[58] Field of Search .............. 364/413.02–413.06; 128/670, 671, 731, 732, 733, 716, 630

[56] References Cited

U.S. PATENT DOCUMENTS

| | | | |
|---|---|---|---|
| 4,776,345 | 10/1988 | Cohen et al. | 128/731 |
| 4,777,962 | 10/1988 | Watson et al. | 128/716 |
| 4,803,997 | 2/1989 | Bowman | 728/671 |
| 4,982,738 | 1/1991 | Griebel | 128/671 |
| 4,999,772 | 3/1991 | Bowman et al. | 364/413.05 |
| 5,047,930 | 9/1991 | Martens et al. | 364/413.04 |
| 5,274,548 | 12/1993 | Bernard et al. | 364/413.02 |

*Primary Examiner*—Lee S. Cohen
*Assistant Examiner*—Robert L. Nasser, Jr.
*Attorney, Agent, or Firm*—Kinney & Lange

[57] ABSTRACT

A sleep analysis system for analyzing a sleep episode of a subject based on measured values of a plurality of parameters characterizing that subject. Portions of the measured parameter signals are classified as significant events, and the significant events are segregated based on parameter signal criteria and time correlation as a basis for the analysis.

30 Claims, 24 Drawing Sheets

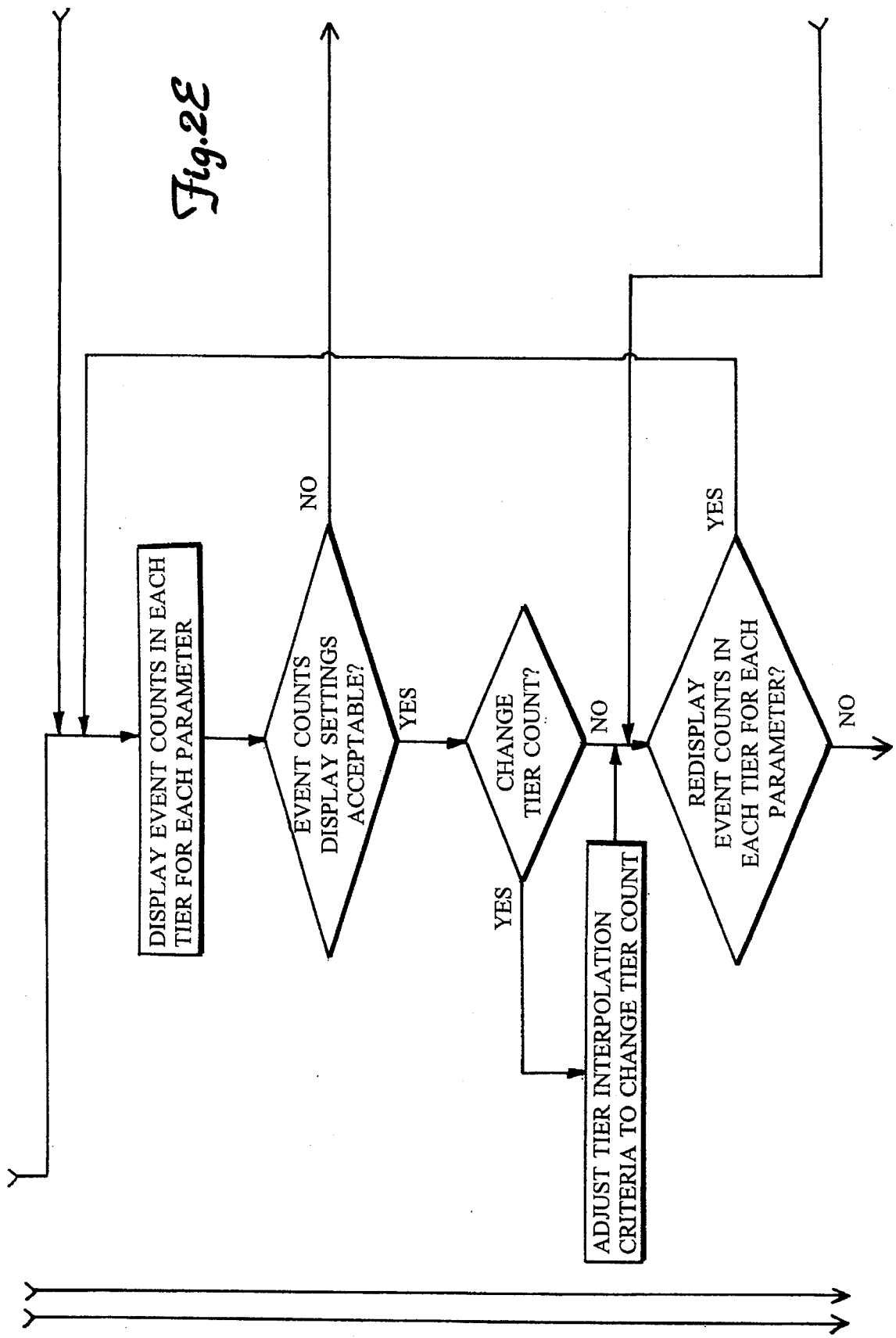

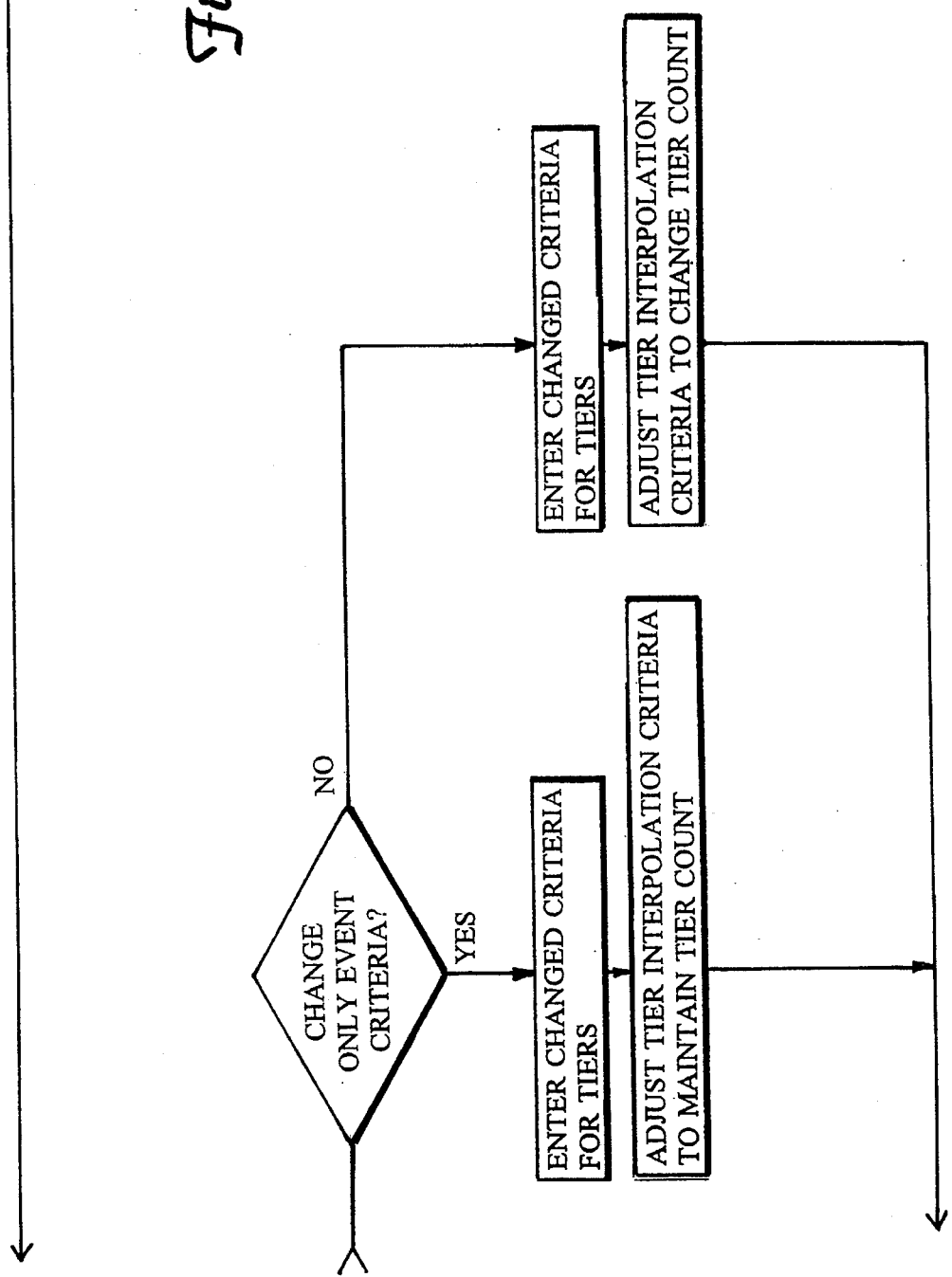

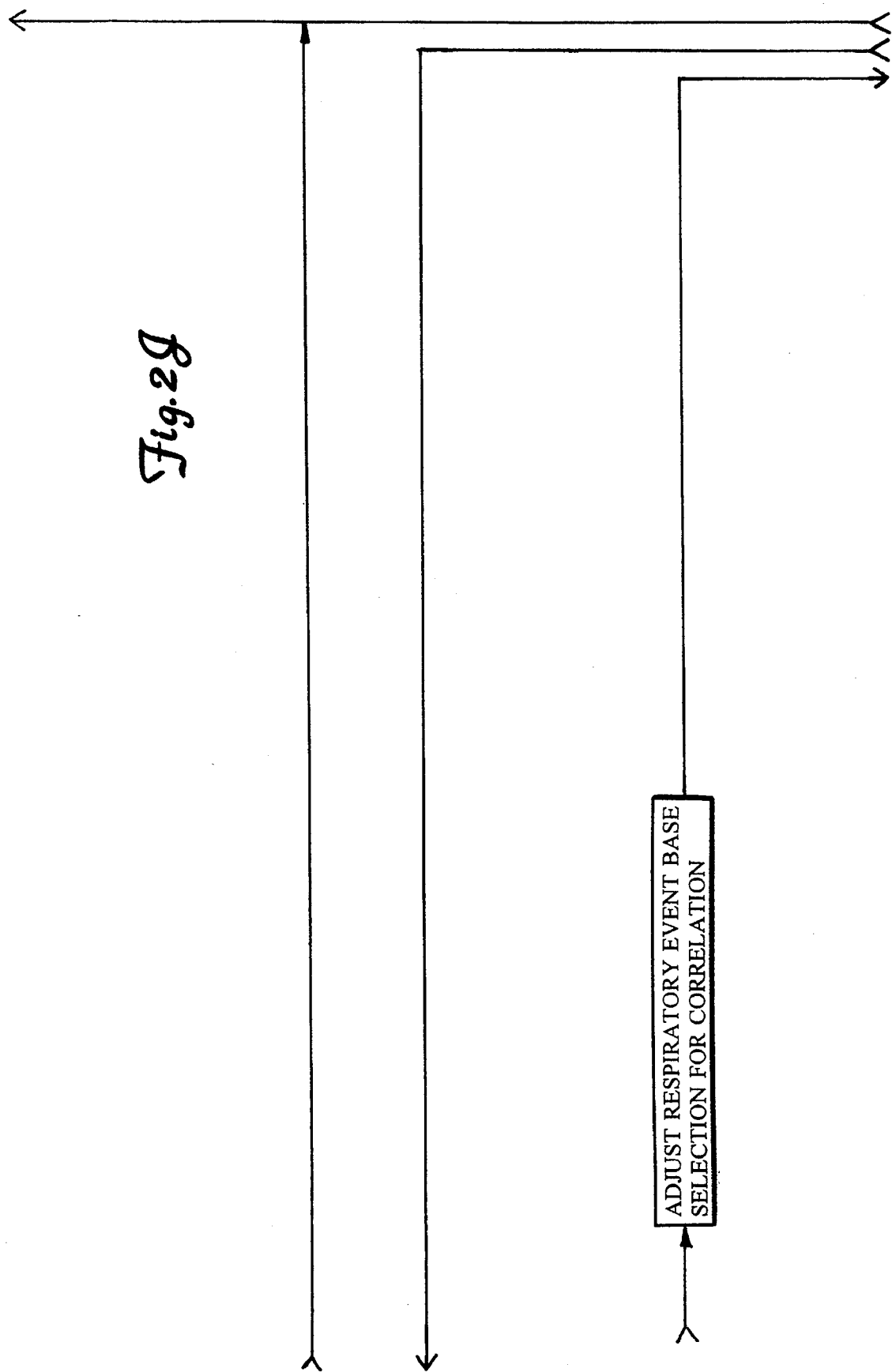

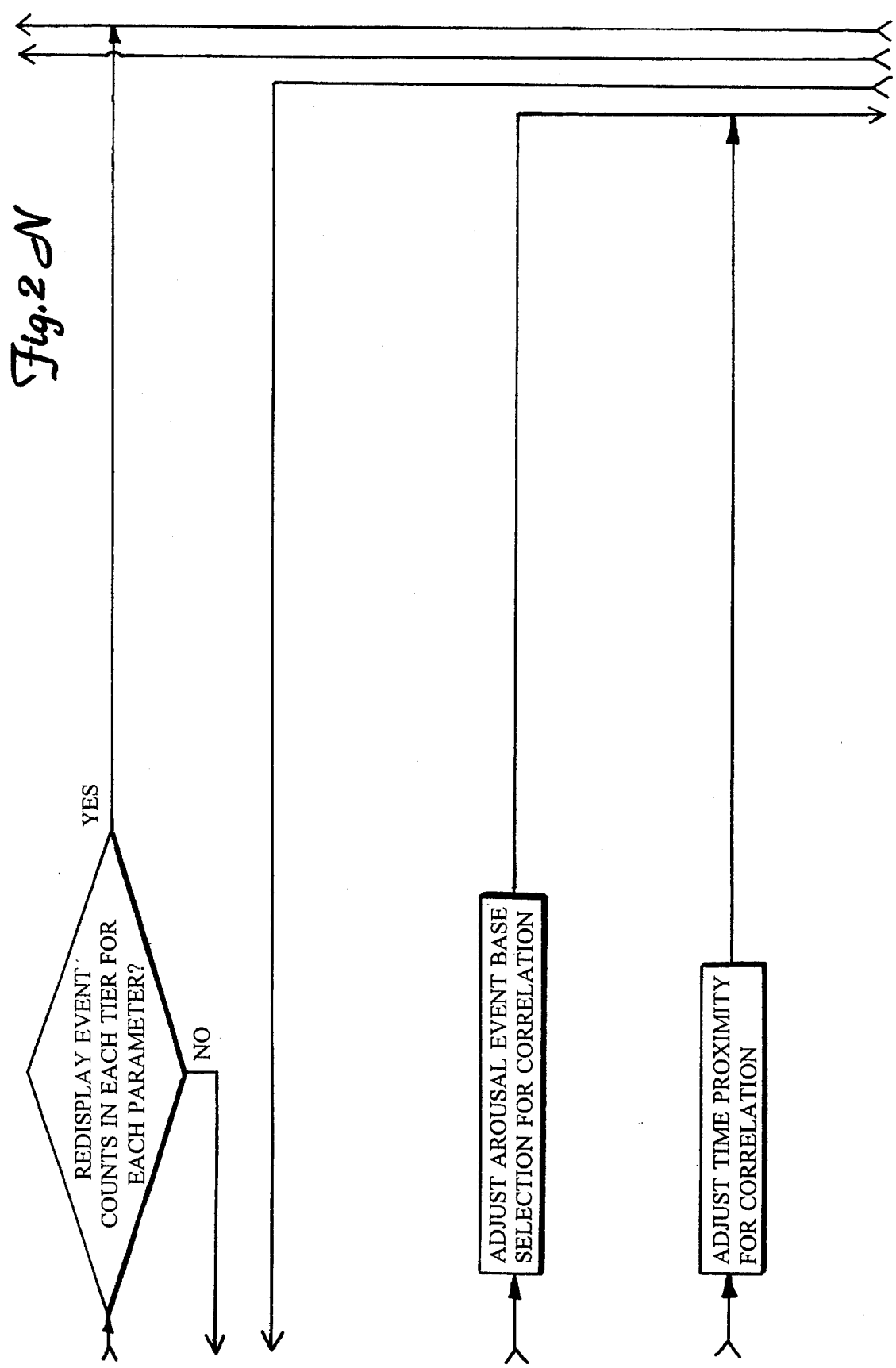

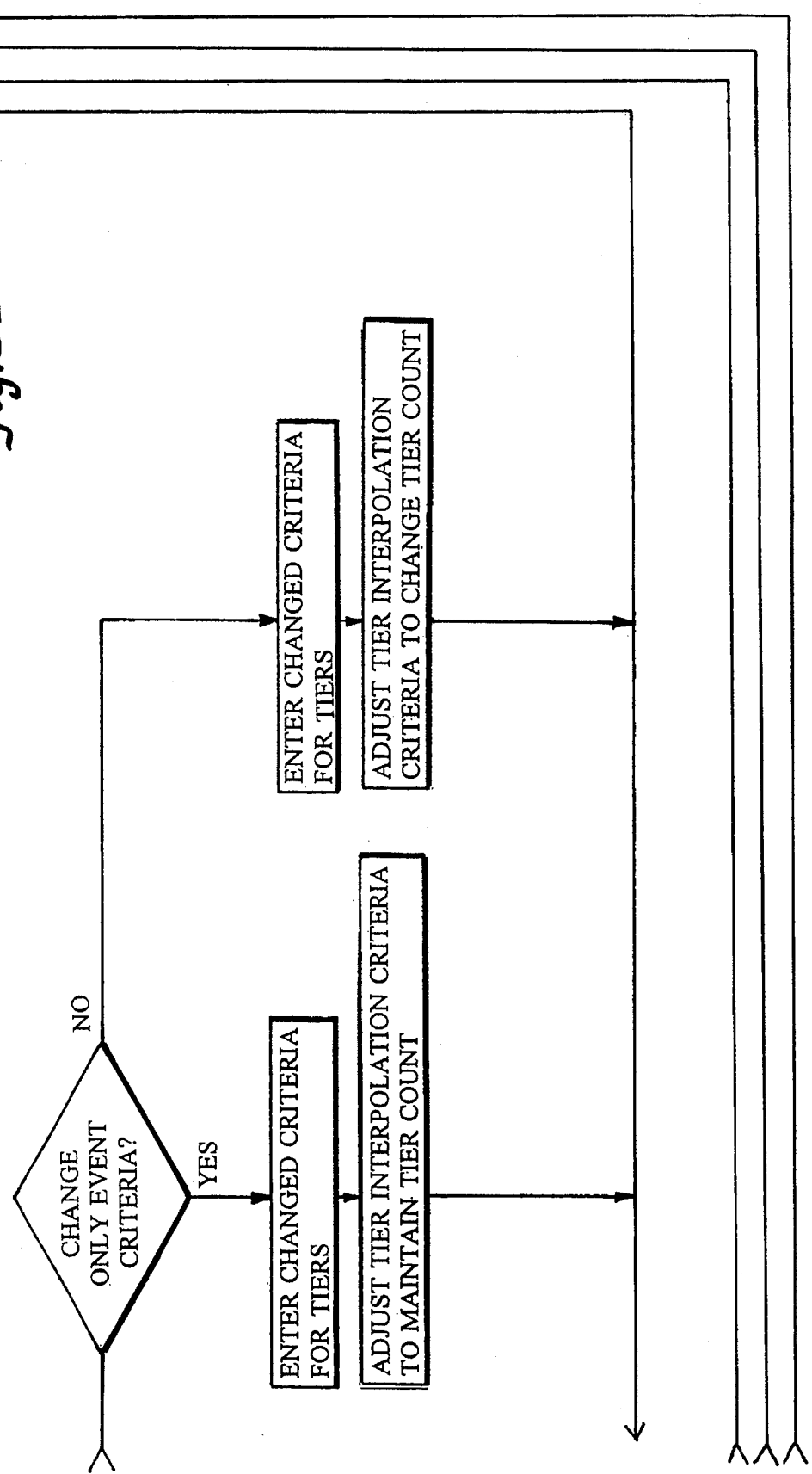

| 𝒜 | ℬ | 𝒞 | 𝒟 |
|---|---|---|---|
| ℰ | ℱ | | |
| 𝒢 | ℋ | | |
| ℐ | 𝒥 | | |
| 𝒦 | ℒ | | |
| ℳ | 𝒩 | | |
| 𝒪 | 𝒫 | | |
| 𝒬 | | | |

Fig. 2 R

ITERATIVE SLEEP EVALUATION

BACKGROUND OF THE INVENTION

The present invention relates to determination of the quality of sleep of a subject under test and, more particularly, determination of that quality from various physiological data obtained from the subject during such sleep.

Substantial research has been undertaken directed toward understanding the nature of sleep and sleep disorders. This research has yielded considerable information concerning human patterns of sleeping and not sleeping, and of physiological activities occurring in humans during sleep. In addition, substantial information has been obtained concerning various sleep disorders.

In assessing the physiological activity occurring during sleep, various kinds of signal data from sensors on the subject are typically obtained, recorded and analyzed. Primary kinds of data obtained for determining sleep disorders are electrophysiological signals such as electroencephalographic signals, and transducer signals resulting from the detection of other kinds of physiological parameters such as signals characterizing respiratory performance. Other commonly measured electrophysiological signals are electrocardiogram signals and electromyographic signals. Other kinds of physiological parameter signals typically obtained by sensing transducers are blood oxygen saturation signals, limb movement or activity signals, and the acoustic signals arising from snoring. Such signals are typically recorded over a substantial duration of the subject's sleep and so provide rather voluminous records.

As a result, computer based storage of such records is attractive, as are computer based analyses of such signal records to determine the occurrence in each of clinically significant events. These significant events in the signal records in such analyses are to be searched for by the computer, and are defined for each particular signal based on criteria specified by the analyst that describe the waveform portion structures of clinical interest in that signal. The computer reviews the physiological parameter signal records that were recorded over the sleeping time of the subject under test to determine which portions thereof meet the specified criteria to thereby determine the occurrence of significant events in that signal. Each such waveform portion thus found in each signal as a significant event therefor is then marked and counted.

Unfortunately, there are no presently agreed upon criteria by sleep analysis professionals, or polysomnographic professionals and technologists, which can be relied upon for each signal record to select all the significant events from each of the signals measured and recorded over the subject's time of sleeping. In fact, there is not yet a general consensus as to what constitutes clinically relevant structure portions in the signals. Furthermore, sleep analysts often are interested in confirming the presence of a significant event in a parameter signal waveform by the closeness of its association with other significant events in other parameter signal waveforms rather than just being interested in the magnitudes of events in the initial parameter waveform. Such an association between significant events in parameter signal waveforms can confirm the occurrence of an event in one of those waveforms even though it may be relatively mild in severity, that is, in magnitude and duration. As an example, respiratory events which appear less severe in the signal waveform obtained for that parameter may still have significant implications if they are associated with electroencephalographic signal arousal events since the resulting sleep fragmentation can cause daytime sleepiness in the subject which can lead to poorer activity performances and to various kinds of accidents.

Such less severe, but clinically relevant, events are recognized by sleep analysts as possibly going undetected if the only detection method therefor is the setting of various thresholds to thereby independently define significant events in each of the parameter signals without regard to events in the other signals. Thus, such analysts often feel forced to review the entire set of polysomnographic signals over time to be certain that no clinically relevant events are lost if such thresholds are set to be quite stringent, that is, to give a relatively high probability of capturing just those signal portion structures which are quite certain to be of clinical interest. Of course, less stringent thresholds could be set to sort significant events from the remainder of the time signals for the parameters being measured, but the result may well be that too many artifacts in the signals are found as events leading to finding too many false positives as significant events. Thus, the analysts again would often feel compelled to review all of the parameter signals over time to eliminate falsely reported significant events in the parameter signals. Hence, there is a desire for a system which can avoid any need to review of all polysomnographic signals over time while providing the user with a cumulation of clinically relevant events in the parameter signals substantially separated from other events occurring in those signals.

SUMMARY OF THE INVENTION

The present invention provides a system for analyzing sleep episodes of a subject through acquiring a plurality of signals occurring during at least parts of that sleep episode representing values of corresponding physiological parameters of that subject. Portions of these parameter signals are classified as significant events for the corresponding parameter based on selected parameter signal criteria, and these signal events are further classified into a plurality of ranks, including an initial rank for a first parameter which contains those significant events based on corresponding signal portions being of a value beyond an initial threshold for that parameter. The significant events for the first parameter are segregated such that a first tier of those events are formed from the initial rank first parameter significant events and those, though not in that initial rank, that occur within a selected time of a selection of significant events of another of the parameters. Others of said first parameter significant events in the plurality of ranks thereof which are not in the first tier are used to form at least a second tier of first parameter significant events. Further tiers can be formed for the first parameter from those events in the second tier by adding suitable criteria therefor, and the tiers for that parameter can be expanded by adding further first parameter significant events thereto which are sufficiently close in time to other selections of significant events of the second or other parameters. Tiers of other parameters can also be formed, and fractions thereof correlated in time with the first parameter can be separately found.

BRIEF DESCRIPTION OF THE DRAWINGS

FIGS. 2A, 2B, 2C, 2D, 2E, 2F, 2G, 2H, 2I, 2J, 2K, 2L, 2M, 2N, 2O, 2P, 2Q and 2R show a flow chart, and a key diagram for assembling the figures to provide a complete chart layout, followed in obtaining, classifying and grouping signal data, and providing operator supplied criteria, in using the system of FIG. 1;

DETAILED DESCRIPTION OF THE PREFERRED EMBODIMENTS

Figure 1:
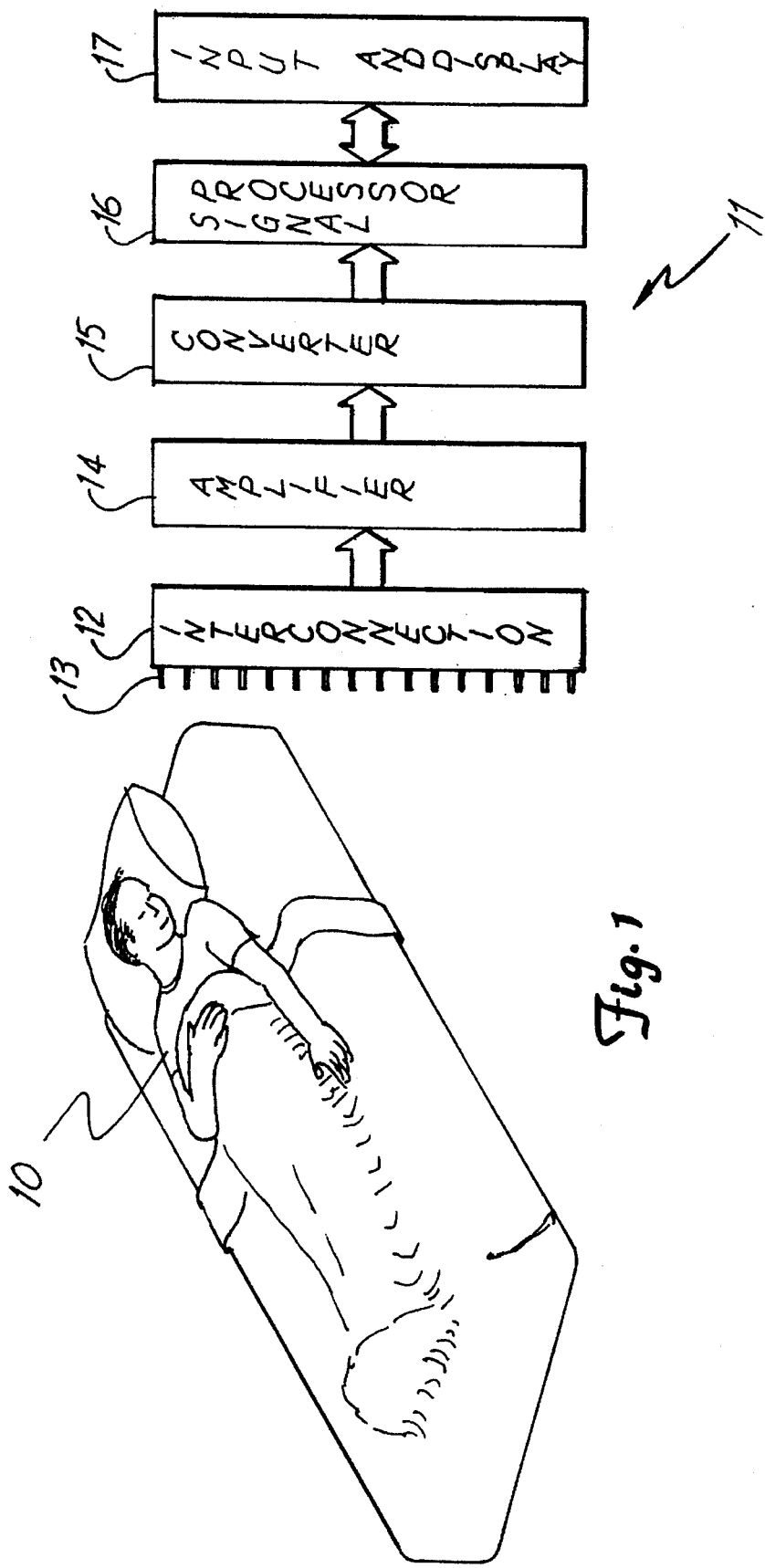
FIG. 1 shows a block diagram of the system of the present invention.

FIG. 1 shows a subject, 10, and a block diagram of a sleep analysis system, 11, for obtaining polysomnographic data concerning several physiological parameters of that subject during a sleep episode in which the sleeping subject has sensors (not shown) attached thereto which respond to these parameters. Such sensors are electrically connected to a sensor interconnection arrangement, 12, by corresponding cables, 13. The sensors provide corresponding parameter signals over time having values representing the behavior of these parameters during that sleep episode time to provide the basis for a report indicating the significant events occurring in those measured parameters over the course of the episode which are used in determining whether any sleep disorders such as apneas, hypopneas, or insomnia occurred. The significant events occurring in the parameter signals are determined not only by finding which portions of those signals went beyond certain threshold values for significant times, but also whether any significant events in some of the parameters occurred sufficiently close in time to confirm that events in a parameter signal which do not meet the threshold criteria may also be clinically relevant events.

Sleep analysis system 11 comprises, in addition to the various sensors, an associated amplifier system, 14, to amplify the analog signals from the sensors and supply them to an analog-to-digital converter arrangement, 15, which includes an analog multiplexer. Consecutive samples, taken over the sleep episode or significant parts thereof, of the amplitude of each analog sensor signal have digital values provided therefor in a well known manner. These digitized samples are provided to a signal processing means, 16, which can be a computer of some sort to process the signals, to extract significant events therefrom, and to apply threshold tests and time correlation tests thereto. In addition, there is a display and input module, 17, so that an analyst can review the nature of the data collected, if desired, and to review the results obtained from the analyses of that date, and to perhaps intervene to cause some reanalysis thereof if reviews of the significant events occurring in the data suggest such an intervention. Typically, a printer is also provided to print out the final report summarizing the findings with respect to the subject whose sleep is being analyzed but that device is not shown here.

FIG. 2 shows a flow chart for the operation of sleep analysis system 11 of FIG. 1, omitting the largely ministerial reporting step. FIGS. 2A, 2B, 2C and 2D represent the start of the sleep analysis process beginning with preparing the subject for such an analysis, including attaching the various sensors thereto, and then obtaining the data for the physiological parameters of subject 10 during sleep through recording the various sensor signals obtained as shown in eight columns of sensing process steps provided from left to right in those figures, one column for each signal sensed and directly used.

The physiological parameter measurement process shown to the far left in FIG. 2A will be described first, and that is respiration which is measurable in various ways. Typically, the measurement need not be an absolute measurement, but rather a relative measurement is sufficient to show whether breathing is occurring or not at times during the sleep episode. One common way of so measuring respiration is by detecting gas flow at the mouth and nose of subject 10, typically with a thermistor or thermocouple. An alternative, or a supplement, is to measure respiratory effort such as by the use of closed volume tubes positioned like belts around the chest and abdomen of the subject to detect circumferential changes in size such as those set out in U.S. Pat. No. 5,191,893 to Reiten and assigned to the same assignee as the present application which is hereby incorporated herein by reference. An alternative for such respiratory effort measurements which gives a more physiologically precise measurement of respiratory effort, is a measurement of changes in pressure in an esophagal balloon which effectively monitors interpleural pressure changes that correlate directly with respiratory effort.

The analog signals resulting from the use of one or more of these sensors is typically amplified and then converted to a digital signal with a typical sampling rate of either 8 or 16 Hz. The resulting sequence of samples forming the digital signal is then examined in sleep analysis system 11 to find significant events occurring therein which are determined based on the average peak-to-peak magnitude change occurring in that signal in each of a succession of selected time divisions together comprising the time duration over which this signal is obtained during the sleep episode. A typical time division duration choice is one second, and so the average peak-to-peak magnitude change for the subsequence of samples in each second of time of that signal is found. Occurrences of significant respiratory events in this signal are those locations on the time axis at which there are sufficient decreases in average magnitude over a sufficient amount of time.

Significant respiratory events are termed apneas if there is essentially no breathing for ten seconds or more. Otherwise, significant respiratory events are termed hypopneas where there is a substantial reduction in breathing for ten seconds or more, but not substantially an outright absence. Sleep analysis system 11 of FIG. 1 has a default setting for determining the significant event of an apnea requiring the average peak-to-peak magnitude of the respiratory signal to be less than 15% of the full scale measurement possible for that magnitude for ten seconds or more. Two default settings are provided in that system for hypopneas, one being the most strict criteria setting to thereby apply the most stringent test as to the occurrence of same, that being a 40% drop in the peak-to-peak magnitude of the respiratory signal lasting ten seconds or more. The alternative, or most lenient criteria default setting for determining a hypopnea is a 15% drop in the peak-to-peak magnitude lasting six seconds or more.

Clearly, the most lenient criteria default setting raises greater questions of whether the respiratory magnitude event is an actual hypopnea or not, while the more stringent criteria default setting leaves less question about whether a questionable hypopnea event has occurred or not. The resulting events are counted and the respiratory information may be displayed by module 17 in alternative manners as indicated by the decision diamonds in the leftmost column of sensing process steps in FIG. 2A. As will be further described below, a display screen exhibited in module 17 that is typically the first view chosen to review the counts of such respiratory events, and selected in the first decision diamond, presents the total number of respiratory events in a first rank which are either apneas or which pass the most stringent criteria hypopnea test, and presents those which only pass the more lenient criteria hypopnea test in a second rank shown above the first rank. Alternatively, screen displays for reviewing the correlation in time of these events with significant events occurring in other parameters can be displayed in the alternative, as selected in the second decision diamond, either for purposes of determining sleep apneas, or for purposes of determining insomnia, as will also be further described below. Only those signal parameters known to be important time correlates for the sleep disorder associated with a particular one of these screens will be represented there.

Figure 3A:
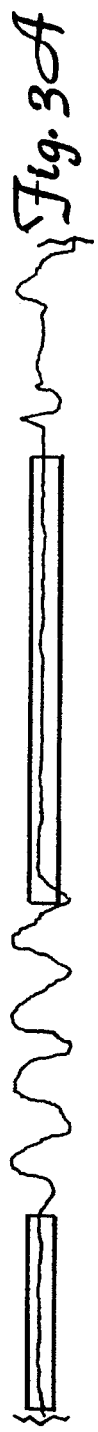
FIGS. 3A, 3B, 3C, 3D, 3E, 3F, 3G and 3H show portions of parameter signals obtained in using the system of FIG. 1.

FIG. 3A shows a typical signal segment obtained by a thermistor from a sleeping subject after digitization. The boxes formed around signal portions show occurrences of significant events of the kind described above.

Figure 2A:
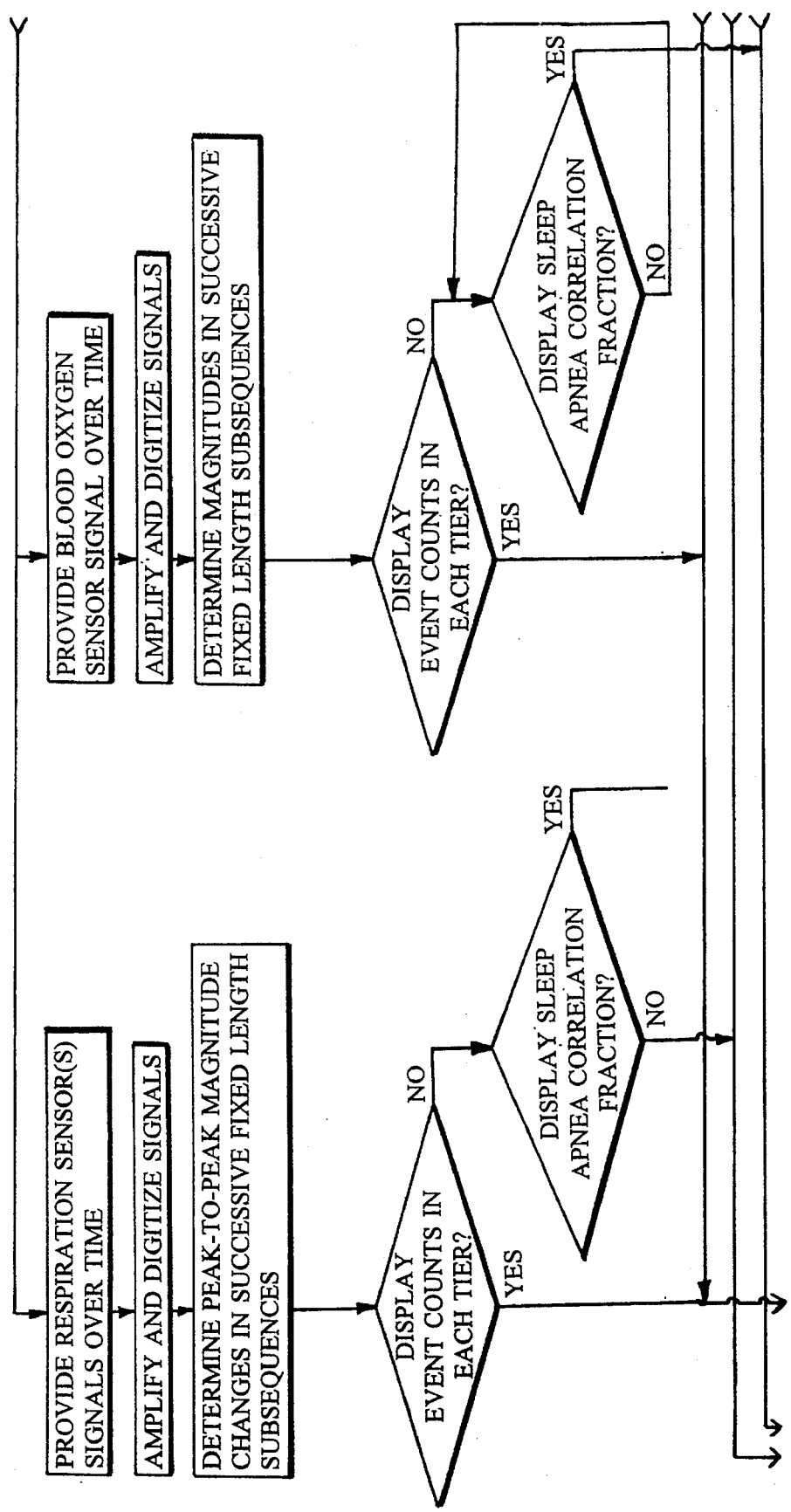

The next column of sensing process steps in FIG. 2A to the right of the respiratory sensing process steps column is for the measurement of blood oxygen saturation. A commercially available saturation blood oxygen sensor is available to place about a subject's finger, and uses infrared pulses as a basis for determining the oxygen saturation, or the fraction of oxyhemoglobin, carried in the blood through that finger. An infrared pulse is passed through the finger on each surge of blood therethrough due to a corresponding heartbeat, and a signal out of the percent of saturation of oxygen in the blood is obtained.

This analog signal from the blood oxygen saturation sensor is sampled 32 times a second in system 11. The digitized signal appears to have relatively little volatility therein unless significant respiratory abnormalities occur which result in the percentage of oxyhemoglobin in the blood being reduced. If such are present, the waveform can look somewhat more sinusoidal since apneas tend to occur in groups reducing the saturated blood oxygen which thereafter returns to the less volatile level occurring prior to the apnea because of the reinstitution of breathing.

The digitized signal obtained is then examined in system 11 to find significant events occurring therein which are determined based on the average value occurring in the subsequences of samples in that signal in each of a succession of selected time divisions together comprising the time duration over which this signal is obtained during the sleep episode. An individual time division choice is two seconds, and so the magnitude average of 64 subsequence samples in every two seconds of time of that signal is found. Occurrences of significant respiratory events in this signal are those locations on the time axis at which there are sufficient decreases in average magnitude over a sufficient amount of time.

Again, default settings in sleep analysis system 11 of FIG. 1 for determining significant events in the blood oxygen saturation signal, termed desaturations, are provided as a pair with the most stringent criteria default setting defining a desaturation event upon occurrences of a 4% drop in blood oxygen saturation lasting ten seconds or more. The most lenient criteria default setting finds such a desaturation upon occurrences of a 2% drop in blood saturation lasting four seconds or more.

Here too, the desaturations are counted, and the blood oxygen information may be displayed by module 17 on the same alternative screens possible for respiratory events as indicated by the decision diamonds in the blood oxygen column of sensing process steps in FIG. 2A except for the insomnia determination screen display. The feedback line about the lower right decision diamond in that column indicates that blood oxygen information is not used in the insomnia determination screen display but only in the sleep apnea determination screen display.

Figure 3B:

FIG. 3B shows a typical segment of a signal obtained in such oximetry measurements after digitization. Again, the boxes indicate significant events in the parameter, here desaturations.

Figure 2B:
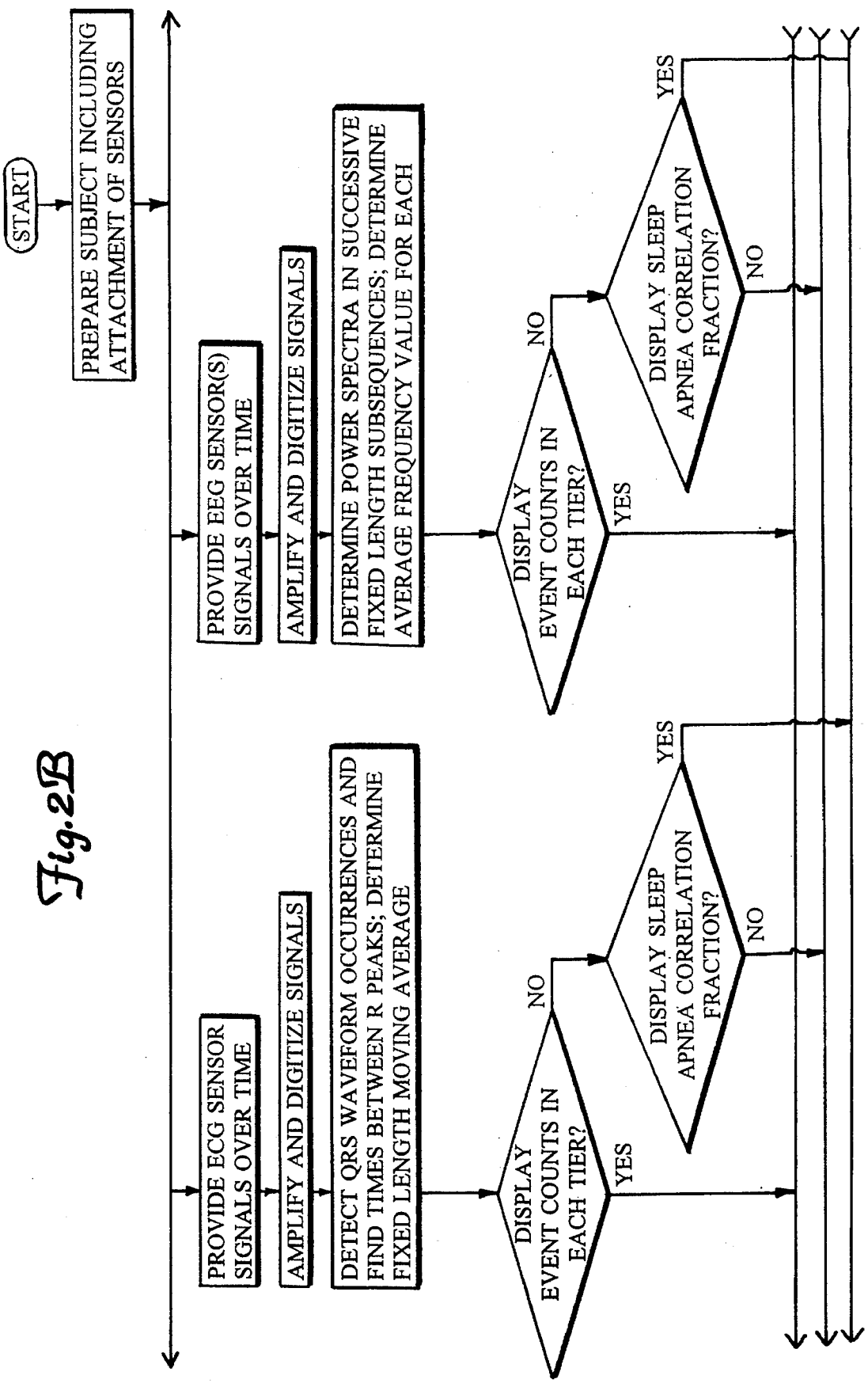

The next column of sensing process steps is shown leftmost in FIG. 2B, and so to the right of the blood oxygen sensing process steps in the flow chart, is for electrocardiogram measurements to determine changes in the rate of heart pulsations or heartbeats, i.e. in the heart rate. Typically, the heart rate slows during an apnea, termed a bradycardic event, and speeds up following the return to more normal breathing, termed a tachycardic event. Such a sequence is called a brady/tachy arrhythmia. In such instances, the well-known QRS waveform complexes in the electrocardic waveform are first increasingly spaced apart in that waveform, and then increasingly less separated. Brady/tachy arrhythmias involving sufficient changes in rates over sufficient time to reach sufficient absolute rates are significant events in electrocardiograph signals. Any commercially available electrocardiograph can be used for this purpose. Typically, just one or two electrodes are connected to the subject's chest for purposes of determining the occurrence of brady/tachy arrhythmia for sleep analysis purpose. The analog signal obtained is sampled at 128 Hz. The heart rate is determined by measuring the time spacings between the R peak of each QRS complex and averaging the same over 16 seconds. This is a moving average with the result provided every two seconds.

Two sets of criteria must be satisfied to have a brady arrhythmia-tachy arrhythmia significant event in system 11 of FIG. 1, and again a pair of these criteria sets are provided for the most stringent and the most lenient significant event defining criteria in providing the default settings therein. The most stringent criteria default setting criteria for finding the occurrence of such a significant event is that there must be a change in average heart rate of ten beats per minute lasting at least ten seconds, and the lowest average heart rate reached in the event must be less than 50 beats per minute, and the highest heart rate in the event must exceed 100 beats per minute. The most lenient criteria default setting for such a significant event is that the change in average heart rate must be six beats per minute lasting more than four seconds, and the lowest average heart rate reached must be less than 60 beats per minute while the highest heart rate must exceed 80 beats per minute.

Once the arrhythmia significant events are counted, the heart rate information may be displayed by module 17 in the same alternative screens possible for respiratory events as indicated by the decision diamonds in the electrocardiogram column of sensing process steps in FIG. 2B. The heart rate significant events information is used in both the sleep apnea and the insomnia screens.

Figure 3C:

FIG. 3C shows a portion of a signal over time from an electrocardiograph for subject 10 during a sleep episode after digitization. Here too, the boxes indicate the bradycardic event portion of the corresponding brady arrhythmia-tachy arrhythmia complex significant event.

Figure 2C:
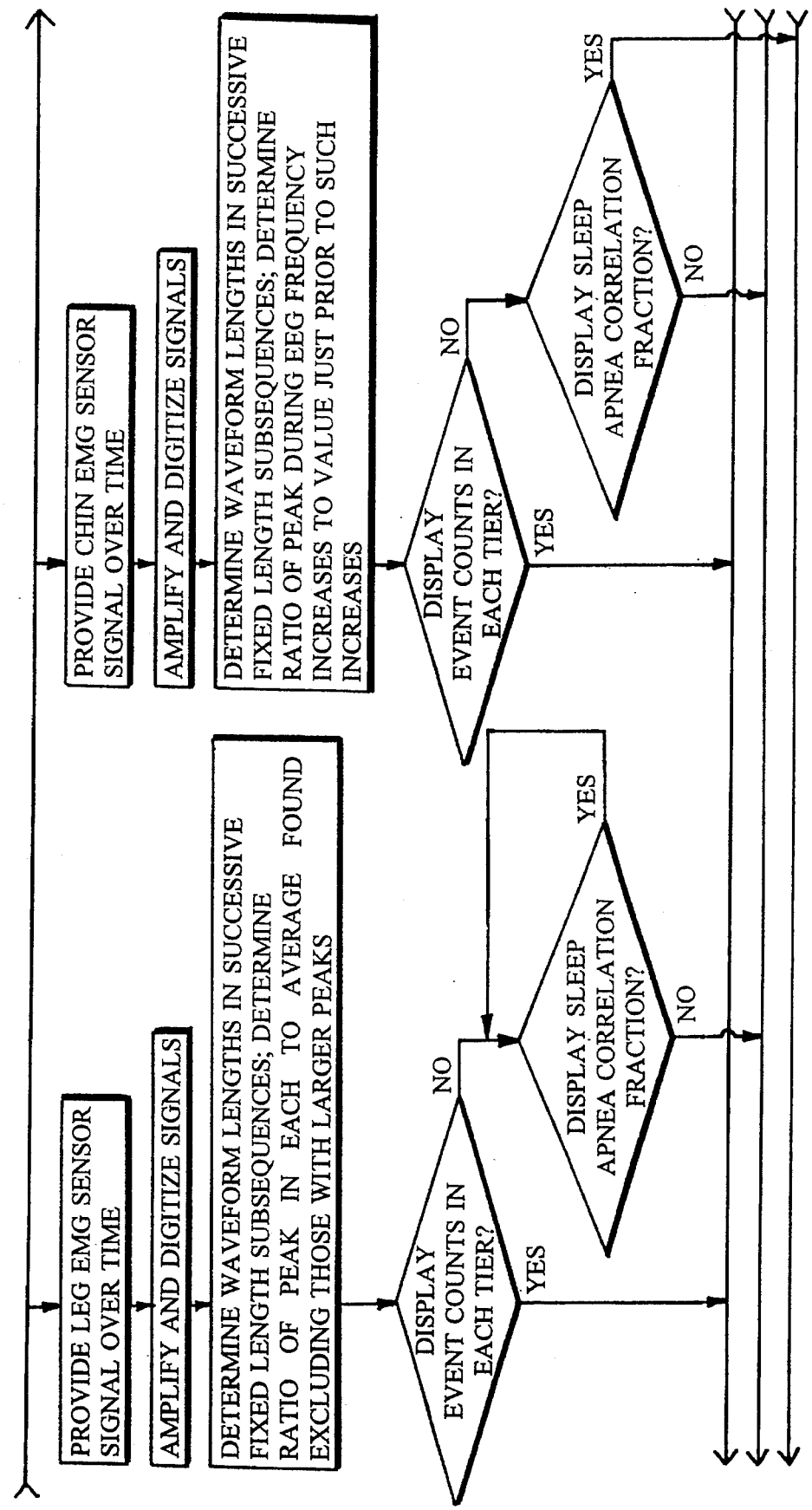

The next column of parameter signal sensing process steps in FIG. 2B involves electroencephalograms, and is used with another column of sensing signal process steps further to the right in the flow chart of FIG. 2 which is presented in FIG. 2C involving electromyograms obtained from the chin of subject 10. These two sensing signals together are used to indicate arousals which are more cerebral type of significant sleep events. However, this aspect of polysomnography is somewhat less clear to professionals in the field and, therefore, some of them tend to associate arousals with additional phenomena such as eye movements or changes in chin muscle activity. Possible wake period arousals are not included unless they occur in the first half of any wake period not preceded by another wake period. Nevertheless, the basic effect in an arousal is an abrupt change in the background activity in the electroencephalographic signal which is in the form of a relatively sharp increase in the average frequency in that signal, and a significant event of arousal in the electroencephalographic signal requires a sufficiently large average frequency change over a sufficient time duration to reach a sufficiently large average frequency value.

If, however, the possible arousal event occurs during rapid eye movement sleep, or REM sleep, as determined by the accompaniment of rapid eye movements measured by electrodes connected to the eye, there must also be a significant change in the chin electromyographic signal for an actual arousal to be found as is more fully described in U.S. Pat. No. 4,776,345 to Cohen et al and assigned to the same assignee as the present application, which is hereby incorporated herein by reference. FIG. 2 does not show a column of sensing process steps for electrooculographic signals as they are not directly used in the sleep analysis determination, but only indirectly used to indicate REM sleep. Nevertheless, such a sensor is used to provide data for this purpose on the system of FIG. 1. The electromyographic signal measure at the chin will have a significant event therein if the magnitude of the change in the total excursion of that signal in one of the succession of selected time divisions during a corresponding increase in the average frequency of the electroencephalographic signal is sufficiently great with respect to the total excursion value the electromyographic signal had in a time division just prior to such a frequency increase.

Any commercial electroencephalographic monitor may be used to obtain the electroencephalographic signal data, and for sleep analysis usually just a single electrode is used in a central position on the scalp such as the C3 position with a reference electrode on an ear such as in the A2 position, positions which are well known in electroencephalographic testing. As implied, the electromyographic sensor for the chin is placed beneath the chin and primarily reflects muscle activity at the base of the tongue. The capability to obtain such a chin electromyographic signal will usually be provided in a commercial electroencephalographic monitor.

Both of these analog signals resulting from these sensors are sampled at 256 Hz. These digitized signals are then examined to determine whether any significant events, arousals, have occurred. The resulting electroencephalographic digital signal sequence of samples has each two second subsequence of samples therein transformed using the fast Fourier transform technique into the frequency domain to obtain the subsequence power spectrum, and then the average frequency of each is found as more fully described in the last reference above incorporated by reference herein. The total "length" of the resulting electromyographic digital signal in each successive two second period, i.e. the total excursion value of the that waveform in that time period, is found by adding the differences together occurring between adjacent subsequence samples for each two second period.

Again, there is a set of default settings used in system 11 of FIG. 1 corresponding to the most stringent criteria which portions of the electroencephalographic and electromyographic signals must meet for a significant event, or arousal, to have occurred in those signals, and another set of default settings for the most lenient criteria for portions of these signals to meet in defining significant events therein. For the default setting reflecting the most stringent criteria, the electroencephalographic signal must have an increase of an average frequency of 2 Hz lasting over at least three seconds and must achieve an average frequency value exceeding 8 Hz but with no maintenance duration at that frequency required. If this occurs during REM sleep, the magnitude of any corresponding change in the chin electromyographic signal total excursion in a time division during the frequency rise must be sufficiently great with respect to the magnitude of the total excursion in a time division just prior to the frequency rise so that a ratio of those two total excursion magnitude values exceeds three. For the most lenient criteria default setting, the rise in an average frequency value must be at least 0.5 Hz lasting over at least three seconds with an average frequency attained as a result of the rise being at least 5 Hz. If the rise in average frequency in the electroencephalographic signal occurs during REM sleep, an accompanying chin electromyographic signal total excursion ratio must again exceed three.

Figure 3D:
Figure 3E:
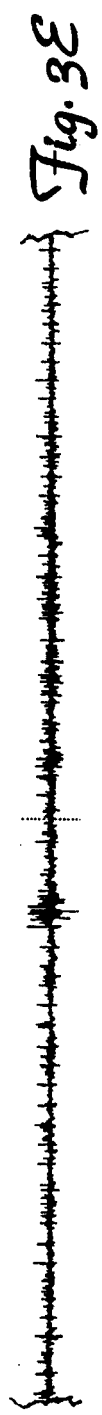

FIG. 3D shows a typical electroencephalographic signal after digitization with again a box marking the occurrence of an arousal event. FIG. 3E shows a corresponding chin electromyographic signal after digitization in which there was a sufficiently active muscle activity occurrence during REM sleep (no box is shown since the event is sufficiently designated in the electroencephalographic signal) to indicate an arousal event has occurred.

The leftmost column of sensing process steps in FIG. 2C, skipped over in describing the electroencephalographic and chin electromyographic signals involved with arousals, shows the steps followed in obtaining electromyographic signals from a sensor connected to the leg of subject 10 for the purpose of determining the occurrence of periodic leg movements. Again, a commercially available electromyographic monitor can be used for obtaining such signals.

Leg movements are known to be causes of arousals, and typically represent neurologic difficulties. These difficulties are not well understood, but the result is that the legs usually jerk repeatedly, typically during the first third of the night, and the jerking of the leg frequently is accompanied by an electroencephalographic arousal to again result in sleep fragmentation. Even a single isolated leg movement of sufficient magnitude is now thought to be clinically relevant in connection with an arousal.

The analog signal obtained from the electromyographic signal monitor is sampled at 256 Hz. The digitized signal resulting must then be examined to find significant events occurring therein which, as for the chin electromyographic signal, are taken to be sufficient changes in motion magnitude from previous motion states, typically situations where the leg of subject 10 was previously at rest. Again, the total excursion value of the leg movement signal in each of a succession of time divisions is the basis for this determination of sufficient leg motion, where again these time divisions in total are the duration of monitoring of the movement of the leg of subject 10 during a sleep episode. The duration of the individual time divisions chosen here is one second, and the total excursion calculated in each of those time divisions in the two minutes of such divisions preceding the one currently under consideration, excluding those that have an excursion that exceeds the criteria threshold, are used to form an average total excursion value as a base line for a magnitude ratio test.

Here too, a pair of default settings in sleep analysis system 11 of FIG. 1 is used for determining significant events in leg movements, the pair having a most stringent criteria default setting defining a leg movement as a total excursion value in the time division under consideration which is more than three times that in the baseline average. The most lenient criteria default setting requires the same ratio to have a value of two.

Some sleep analysts consider periodic limb activity only if there are sufficient number of consecutive movements rather than a single isolated movement. In that situation, the most stringent default setting test may also have the added requirement that there be at least four consecutive movements within a minimum of four seconds between and a maximum of 90 seconds between such movements. The least stringent test would again require only a single isolated leg movement.

Such leg movements are again counted and the information displayed by module 17 with the same alternative screens being available for such leg movement significant events as indicated by the decision diamonds in the leg movement column of sensing process steps in FIG. 2C except for the sleep apnea screen display. The feedback around the second decision diamond in that column indicates that leg movement information is not used in the sleep apnea screen display but only in the insomnia screen display.

Figure 3F:

FIG. 3F shows a typical part of a signal obtained from the electromyographic monitor measuring leg movements after digitization. The boxes are used again here to indicate some of the significant events in the parameters.

Figure 2D:
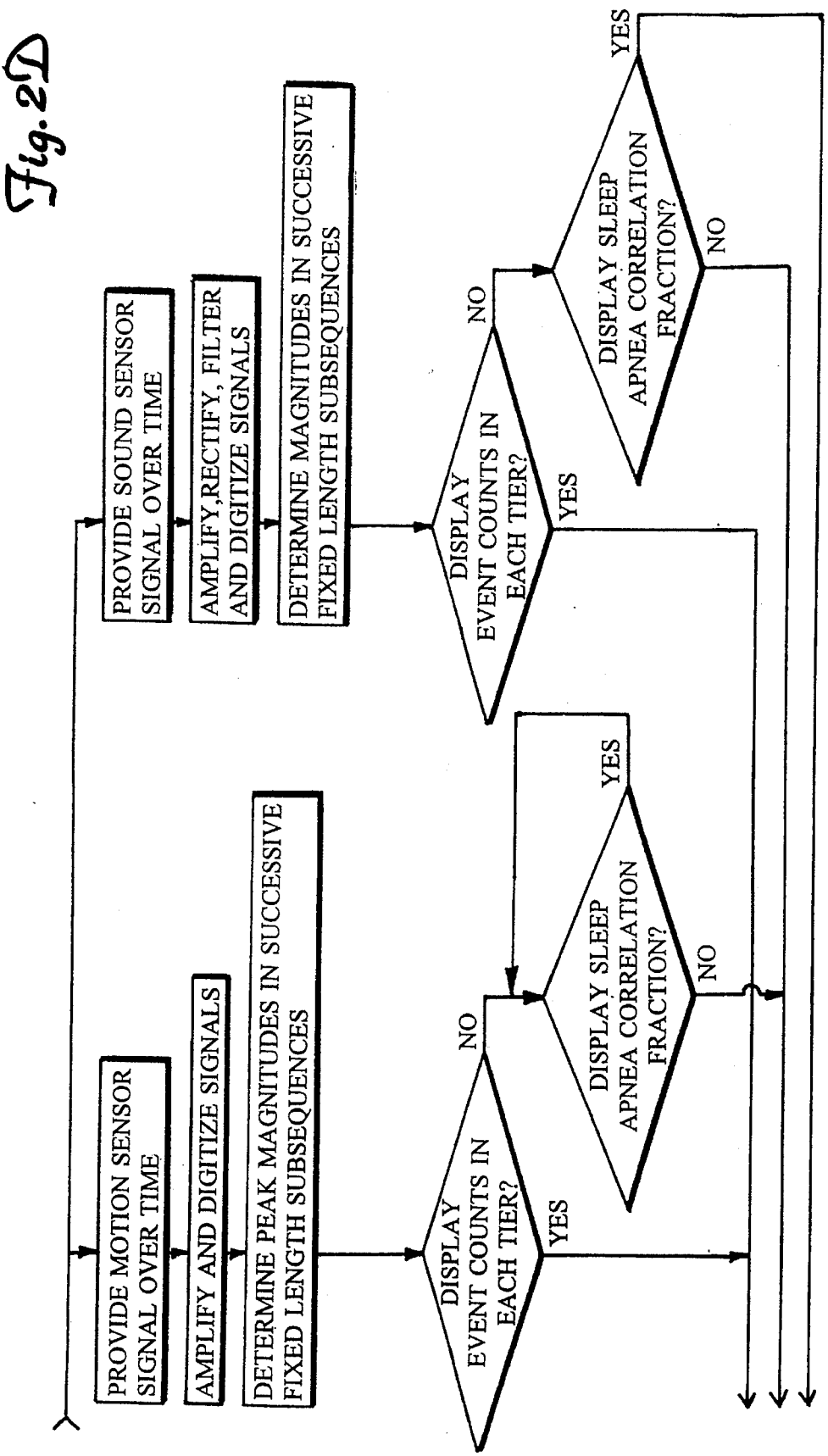

In addition, other limb movement activity is of interest in connection with arousals and the resulting sleep fragmentation. Thus, the leftmost column in FIG. 2D shows the column of sensing process steps followed in determining motion of an arm of subject 10. The motion sensor used is an accelerometer attached to the wrist of subject 10, and the analog signal provided thereby is sampled at 8 Hz. The examination of this signal for significant events involves determining whether the peak amplitude reached is sufficiently far from a baseline value, here typically the rest value of essentially zero, in each of the succession of time divisions which together comprise the duration of this measurement during a sleep episode. The individual time division duration chosen is two seconds. The most stringent and least stringent criteria default settings for sleep analysis system 11 of FIG. 1 are that the peak acceleration must exceed 50% of full scale measurement possible to be a significant event or, in the least stringent instance, must exceed 10% of full scale measurement possible to be a significant event.

Such significant events are again counted, and the information may again be displayed by module 17 on the same alternative screens possible for respiratory events as shown by the decision diamonds in the leftmost column of FIG. 2D except for the sleep apnea screen display. Again, the feedback path around the second decision diamond indicates that limb motion information is not used in the sleep apnea determination screen display but only in the insomnia determination screen display.

Figure 3G:

FIG. 3G shows a typical segment of a signal obtained in such a limb movement measurement alter digitization. Once again, a box indicates a significant event occurring in the parameter signal.

Finally, the last column of sensing processing steps are shown to the far right in FIG. 2D, and concerns acoustic sensing of sounds emanating from the vocal tract of subject 10, primarily snoring sounds This sound is acquired by a tracheal microphone provided at a submandibular position on subject 10 during the sleep episode.

Studies have shown that snoring, associated with oscillation in supraglottic pressure and air flow, is often related to obstructive sleep apneas as opposed to central apneas. However, snoring is also found associated with changes in flow and supraglottic resistance not accompanied by evidence of obstructive sleep apnea or significant desaturations. Nevertheless, studies show that excessive daytime sleepiness and lack of alertness often occur in those who snore heavily, and that such snoring is related to arousals.

The analog signal obtained from the microphone is amplified, rectified and filtered using an envelope detector, and the resulting analog signal is sampled at either 8 or 16 Hz. This signal is examined for significant events by determining the magnitude change in that signal in each of a succession of time divisions which together comprise the duration of sound monitoring during the sleep episode. The individual time division duration typically chosen is one second, and thus the digitized signal magnitude change is determined each second.

A most stringent criteria default setting and a least criteria stringent fault setting are again provided in sleep analysis system 11 of FIG. 1. The most stringent criteria setting requires that the digitized signal have a magnitude increase greater than 40% of the full scale measurement possible, while the least stringent criteria default setting requires that the magnitude increase in the digitized signal exceed 20% of the full scale measurement possible.

The significant events of sufficient sound increase are counted, and the information can be displayed in module 17 on the same alternative screens as possible for respiratory events as indicated in the decision diamonds in the sound monitoring column of sensing process steps in FIG. 2D. That is, the sound information can be used in both the sleep apnea determination screen display and the insomnia determination screen display.

Figure 3H:
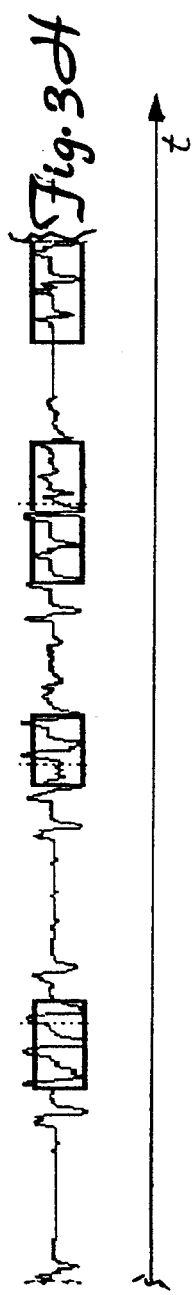

FIG. 3H shows a typical segment of a signal obtained in such sound measurements after digitization. Here too, boxes indicate significant events in the parameter.

The uppermost decision diamonds in each of these columns of sensing signal processing steps in FIGS. 2A, 2B, 2C and 2D route the significant event count information of each parameter signal to the first display step block shown at the top of FIG. 2E. There is implemented the display of the totals of each of these counts for the corresponding parameter signals excepting the electroencephalographic signal and the chin electromyographic signal (and the electrooculographic signal though not shown) as the information in these signals is combined to provide the total count of the parameter termed arousals. The display screen provided to show this full complement of parameter signals significant event count totals is the usual first display viewed by a sleep system user, but the user can go to either of the sleep apnea determination or insomnia determination display screens directly if desired, as is shown in the lowermost of the decision diamonds in these sensing signal process step columns. The following description assumes that the first display viewed will be the usual one, that is, the one indicated in the first block in FIG. 2E.

Figure 4:
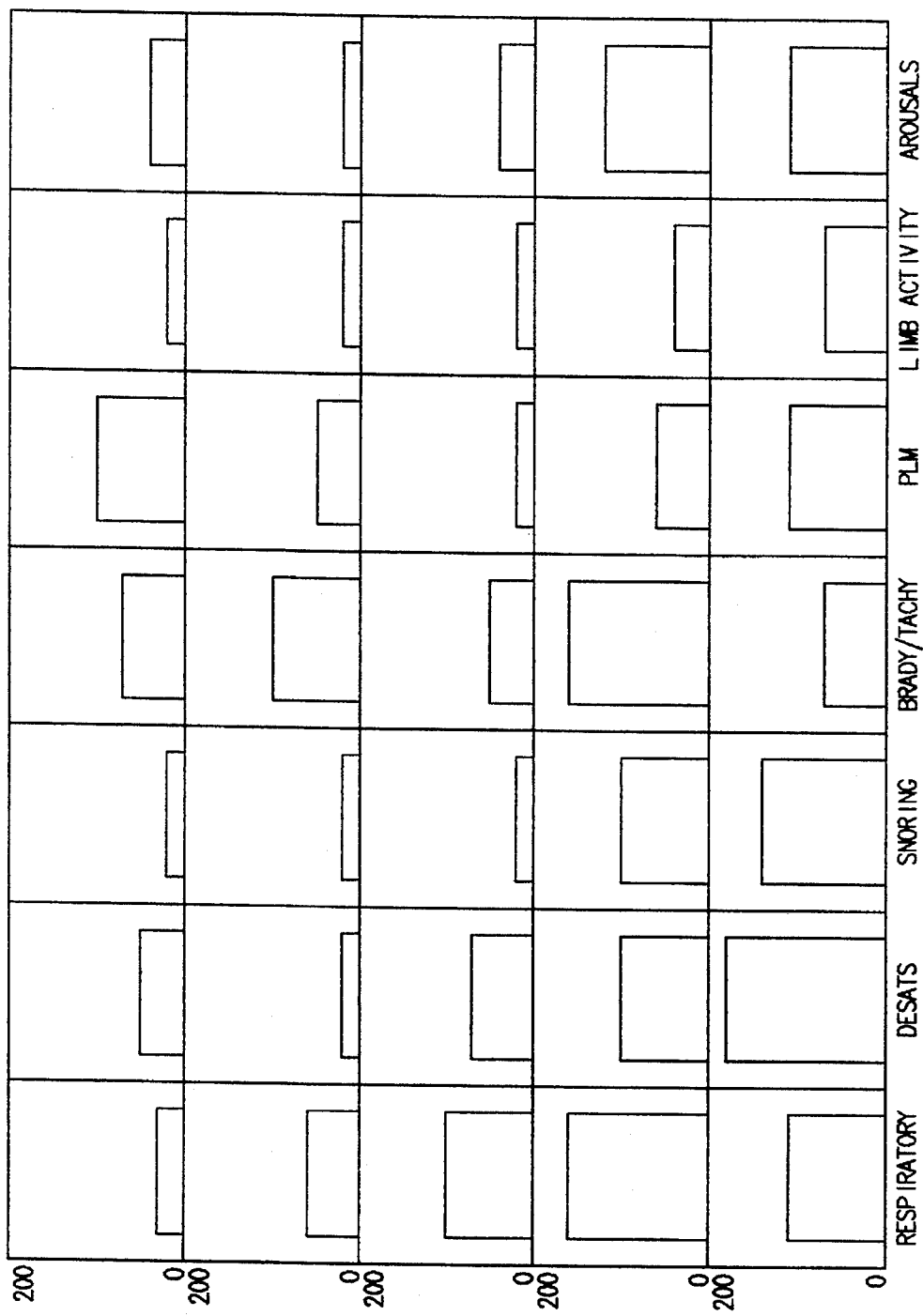
FIG. 4 shows a display used with the system of FIG. 1.

An example of a resulting screen in such a display is shown in FIG. 4 which represents the significant events total counts for the full complement of parameters. In that figure, the lowest row in the screen presentation is a bar graph extending from left to right with each bar representing significant event count for a corresponding one of the parameter signals, or the combination of parameter signals used to indicate the occurrences of arousals. The counts represented by each of these bars in the graph are those of significant events for that parameter which exceed the most stringent criteria default setting requirements for that parameter. The vertical axis of counts for this bar graph extends from zero to 200, as indicated on the left in that figure.

Since there was only one other default setting described for each parameter, the least stringent criteria default setting, the remaining four rows, each representing a corresponding bar graph similar to that of the first row, have, in any column including all four of these remaining rows, the cumulative significant event count totals corresponding to the column parameter that meet the least stringent criteria default setting but which do not meet the most stringent criteria default setting. Rather than having just one further row with one further bar graph as a single most lenient criteria default setting would seem to imply, system 11 can linearly interpolate between the most stringent and the least stringent criteria default settings so that the significant events satisfying the least stringent criteria default setting, but not the most stringent, can be divided into two, three or four additional different ranks through using the linear interpolation process capability provided in system 11. This allows the operator of system 11 to explore where the concentration of significant events is located in the range defining the criteria between the least stringent criteria default setting and the most stringent criteria default setting.

In addition in system 11, the default settings can be changed by a user who so desires, thus changing the count totals in the various ranks of significant events shown along the columns in the full parameter complement screen of FIG. 4. Reducing the most stringent criteria for the parameter associated with a column will increase the number of significant events ranked in the lowest row of that column in FIG. 4 while decreasing those in the higher rows of that column, assuming that the least stringent criteria are not changed. In addition, rather than changing the default settings in system 11, the criteria settings for determining whether significant events are to be ranked in the lowest row or in one of the other rows can be superimposed over the default settings by the system user, thus leaving the default settings as they were when applied to each subsequent ensemble of data obtained from other subjects, or other sleep episodes of the same subject, but changing the rankings for events in the current data ensemble.

Hence, in FIG. 2E below the first block therein for the displaying step, decision diamonds and other blocks in that figure, and in FIG. 2F, allow changing the criteria by which significant events are defined, and so by which they are ranked in the various row bar graphs. The first decision diamond below the display block in FIG. 2E is for determining whether the display settings are acceptable. If not, the decision diamond in FIG. 2F determines whether significant event criteria are to be changed along with the changing the number of interpolative rows ("tiers") in the full parameter complement screen of FIG. 4, or whether the significant event criteria will be changed while leaving the number of interpolative rows unchanged. With either choice, the corresponding changes are implemented in the appropriate one of the two pair of entry and tier adjustment blocks shown in FIG. 2F below that decision diamond. Returning to FIG. 2E, the system user then determines whether the full parameter complement screen is to be redisplayed in the lowest decision diamond in that figure by returning to the display block at the top of the figure.

Also in that figure, if the significant event criteria, including default settings, are instead accepted in the decision diamond below the display block at the top, the number of interpolative rows alone may be changed as determined in the second decision diamond below that display block which, if such a change is decided upon, is implemented in the tier adjustment block to the left and below that decision diamond. The system user can then decide to view the result of such a change in the full parameter complement screen of FIG. 4 if desired, this decision occurring in the lowest decision diamond in FIG. 2E and implemented through returning to the display block at the top of that figure. If no such change in the number of rows shown in the display is desired, the system user proceeds directly to determine whether the screen should be redisplayed (or continued to be displayed), or not, in the lowest decision diamond shown in FIG. 2E again implemented by being returned to the display block at the top of that figure.

In making such significant event criteria setting changes, and perhaps especially in making any default setting changes for these criteria, the system user may be aided in seeing portions of the digitized parameter signals over time obtained for each parameter, sample portions of which have been shown in FIG. 3. Corresponding flow chart process steps for doing so are set out in FIGS. 2G and 2H where such a determination is made in the first decision diamond to the upper left in FIG. 2G as to whether the system user wishes to inspect such digitized signals over time, after deciding to end the display of the full parameter complement screen in the lowest decision diamond in FIG. 2E. If so, a display thereof is provided through the display block step to the right of that first decision diamond in FIG. 2G. The remainder of FIGS. 2G and 2H allow changing of the significant event criteria, again in effect superimposing new criteria over the default criteria, or changing the number of rows shown in the full parameter complement screen of FIG. 4, or both. Such changes are implemented through the remaining decision diamonds and change blocks in these figures just as they are in matching decision diamonds and blocks of FIGS. 2E and 2F.

Figure 2G:
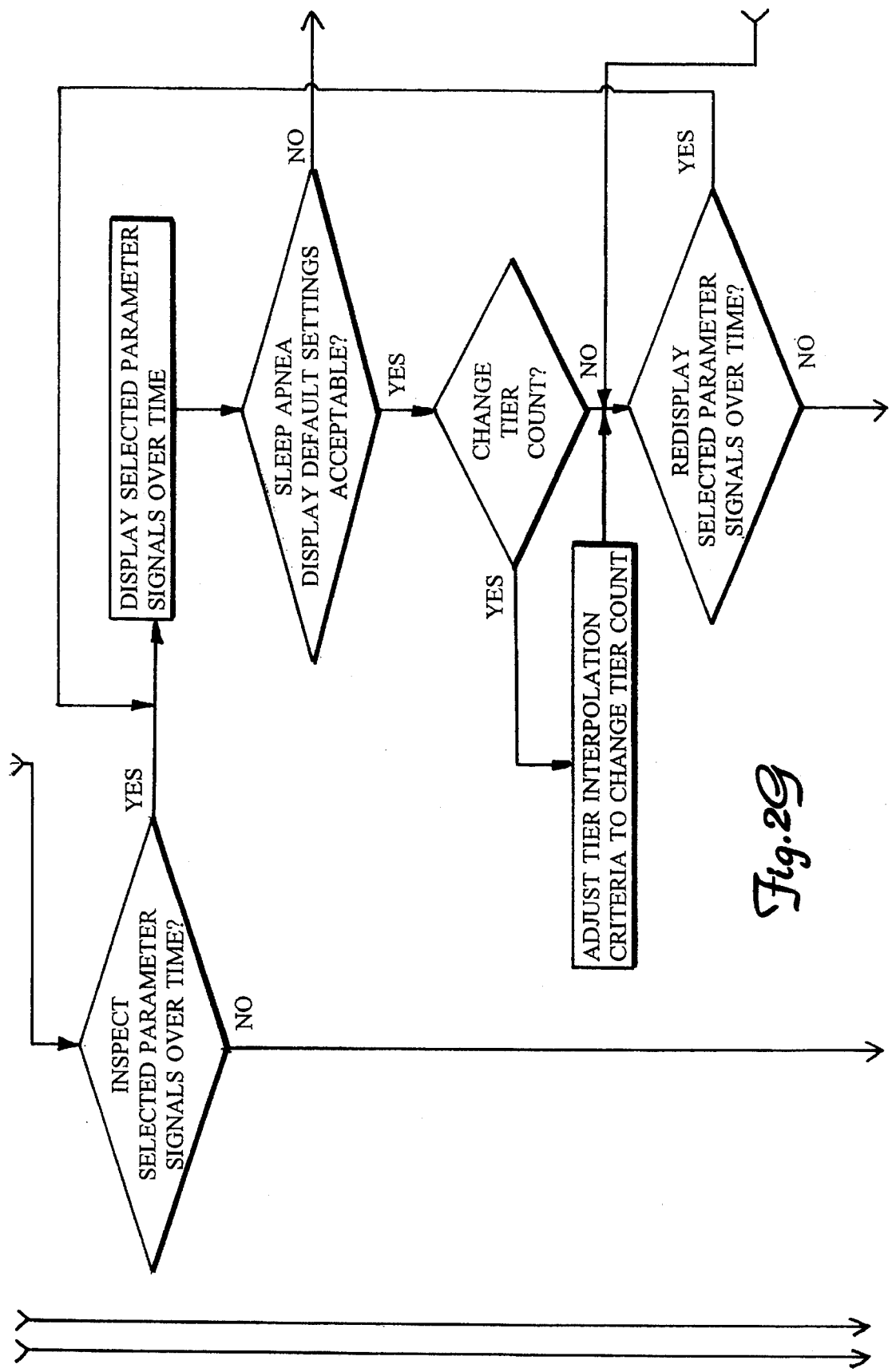
Figure 2H:
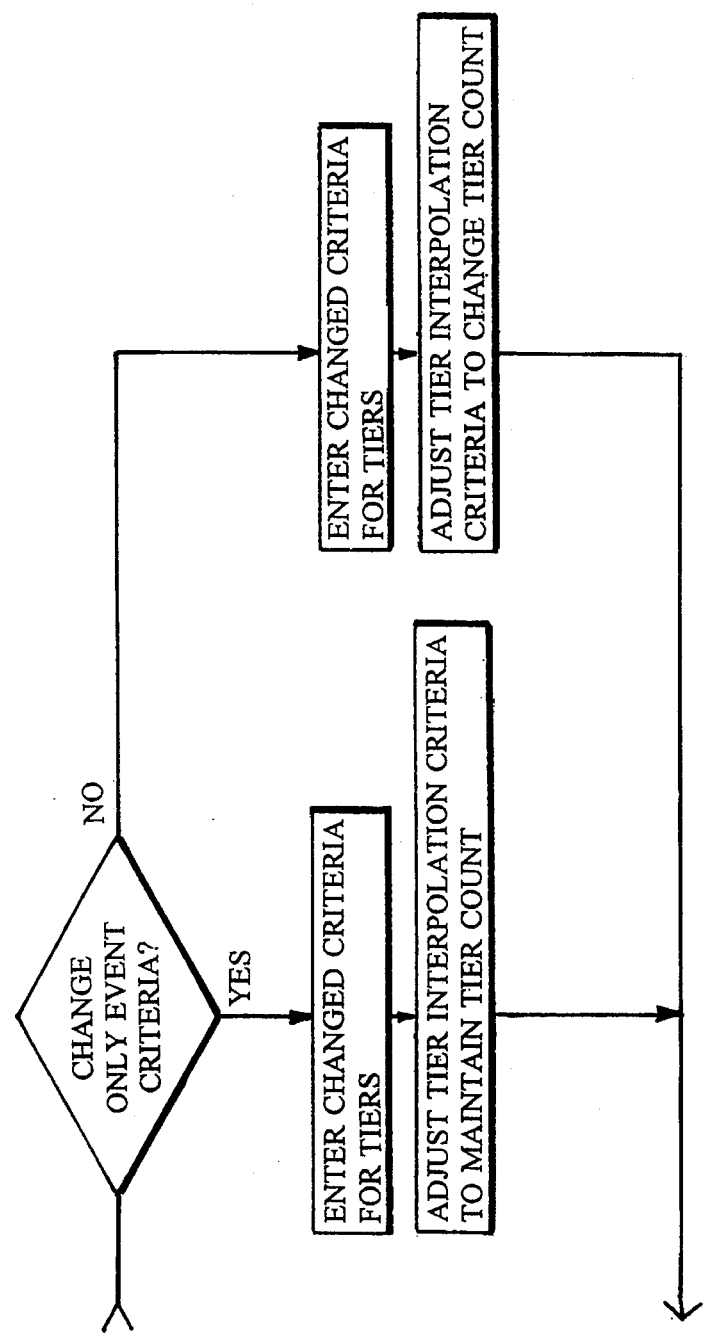
Figure 2I:
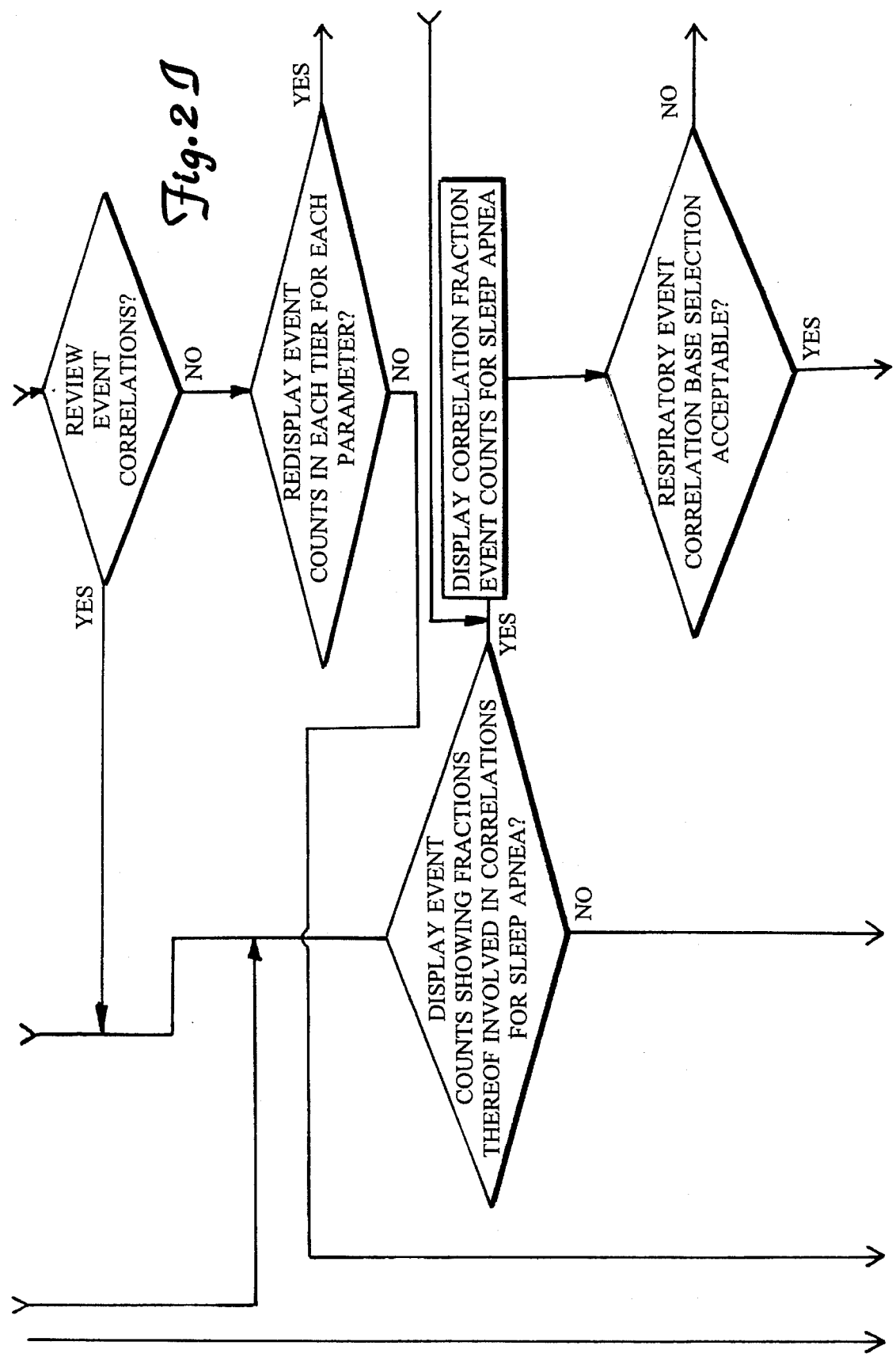

The lowest decision diamond shown in FIG. 2G allows redisplaying the digitized parameter signals over time after any such changes are made, if desired, through returning to the display block at the top of that figure. If not so desired, FIG. 2I shows that two further decisions are possible in connection with inspecting the digitized parameter signals over time in the succession of two decision diamonds encountered following a NO decision in the lowest decision diamond in FIG. 2G. Those two decisions are whether to review significant event correlations as indicated in the uppermost decision diamond in FIG. 2I and, in the decision diamond therebelow in that figure, whether to redisplay the full parameter complement screen of FIG. 4 after any changes made in FIGS. 2G and 2H.

The decision involving event correlations, and the use of the word "tier" in connection with the decisions and implementation of the choices as to the number of rows to be displayed in the full parameter complement screen of FIG. 4, as set forth in FIGS. 2E, 2F, 2G and 2H, are related to the capability in system 11 to superimpose significant event criteria settings over the default settings described above. If only the corresponding most stringent criteria default setting is used to determine the presence of significant events for each of the parameters, the system user will be unaware of just what the potential significant event situation is. Thus, if the blood oxygen saturation significant event is defined as a drop of 4% or more lasting ten seconds or longer, then the blood oxygen saturation parameter signal portions which meet or exceed these requirements will, of course, be detected and displayed. However, the user would be unaware of any desaturation events corresponding to signal portions which had a drop of 4% in blood oxygen saturation but lasted only nine seconds. Missing potentially significant events creates a quality assurance problem if the system user intends to use only the significant events selected by the most stringent criteria as a basis for interpretation of the sleep patterns of subject 10 and for the diagnosis of any disorders.

This situation, as previously indicated above, has often led users of sleep analysis systems limited to finding just one group of significant events for a parameter to believe they are forced to review the entire set of parameter signals over time to be sure that they understand the data with respect to potentially significant events, since at least some of those events may well have to be included in the group found if there is to be an accurate interpretation of the meaning of the data obtained. Thus, as described above, two default settings are used in system 11 so that the most lenient criteria setting captures for attention of the system user an additional selection of significant events which are potentially clinically relevant. In addition, other setting levels can be provided between the most stringent criteria default settings and the least stringent criteria default settings (through, as described above, linear interpolation between these criteria both as to time durations and magnitudes). This capability permits the user to view a spectrum of ranks of increasingly severe significant events beginning with the rank in the top row of the full parameter complement screen of FIG. 4 and moving downward with increasing severity to reach the rank in the lowest row shown there which has the most severe parameter signal structure portions as selected by the most stringent criteria default (or superimposed) settings. Hence, the default settings rank the various significant events for each parameter into as many as five ranks of increasing severity from top to bottom as shown in the screen of FIG. 4.

Such a display screen clearly informs the system user of the presence of milder significant events in the corresponding parameters at a variety of severity levels without the need to reanalyze the data using several further sets of criteria as would be required for sleep analysis systems able to find only a single group of significant events for each parameter. This feature is very beneficial for the system user in assuring a quality of interpretation and diagnosis. If there are no or few events at the most severe rank but many at less severe ranks above in the display of the screen of FIG. 4, the system user will know to inspect the data further to determine whether the events detected at a milder level of severity are clinically relevant. Alternatively, if the great majority of the significant events detected are displayed at the most severe rank, then further viewing of the data is relatively pointless and the reported number of clinically significant events in the most severe rank is quite accurate.

However, the grouping of significant events for each parameter into count totals over the duration of the measurement of parameter signals during a sleep episode results in the loss of the time base information for these events, and so loss of the ability to see how closely associated in time is the significant event for one parameter with that of another.

Thus, although the system user is made aware of the presence of less severe significant events by the rankings shown in the full parameter complement screen of FIG. 4, that user does not know whether the significant events of different parameters (in the different columns of the screen of FIG. 4) are associated with one another sufficiently closely in time to form a complex of time related significant events. Such knowledge is especially important for data ensembles from subjects where most of the significant events are detected at severity levels other than the most severe since these events have a significantly greater probability of being false positive events due to the presence of various artifacts in the parameter signals. The determination of whether many of these significant events are actually truly significant in a clinical sense is much aided by the use of further screen displays showing correlations in time between parameter signal significant events which can serve to establish that milder significant events are truly clinical relevant because of their associations with one or more other parameters in time.

Through viewing the correlation in time of significant events for the primary factors on which determinations of the occurrences of the sleep disorders of sleep apnea and insomnia are based, respiratory significant events and arousal significant events, respectively, with significant events occurring in other parameter signals, the system user can more quickly determine the best criteria setting for inclusion of additional significant events in the lowest row of the full parameter complement screen of the display shown in FIG. 4. The significant events included in this row are to be those severe enough to have clear clinical relevance to thus be the basis for interpretation of the data obtained in the analysis of the sleep episode of subject 10. If, for instance, the group of significant events included in the second row of the screen in FIG. 4, the next less severe rank of events, under the desaturations column has a large fraction thereof which correlate in time with respiratory events in another column, the system user may well conclude that these desaturations are also significant events of clinical significance and, therefore, will change the criteria from those for the default settings for the most severe group of desaturation significant events to other values in superimposed settings (or change from previous superimposed settings to new ones) to substantially include therein (to form a "tier" of most severe significant desaturation events) those previously included in the next less severe rank of events which would otherwise be excluded from the most severe group and adversely affect determinations of sleep apnea disorders. System 11 can alternatively itself be set to review correlates and include some fraction or all of them in the most severe group of significant events. Similarly, such inclusions can be provided for the other parameters involved in, and the primary parameter involved in, determining occurrences of sleep apnea, at least to the extent that correlation with respiratory events is a strong indicator of there being significant events associated with those parameters that are clinically relevant even though their magnitudes or durations would have otherwise precluded them from being in the group of most severe significant events. In the same manner, such inclusions can be provided for the other parameters involved in determining the occurrence of insomnia in being correlated in time with the primary parameter involved in that determination, arousals.

Similarly, if correlations in time are investigated by the system user for the ranks of respiratory events as the primary determinative parameter for sleep apnea, or for the ranks of arousal events the primary determinative parameter for insomnia, a large number of significant events in the less severe ranks of those primary parameters which are correlated in time with the other parameters important in determining sleep apnea and insomnia, respectively, may also indicate that those milder significant events should also be added to the significant events included in the most severe group of significant events for these primary parameters. This might be determined, for instance, by viewing the correlation in time between the significant events in the second row of the respiratory column, the next less severe rank of events after the most severe rank, and determining the correlation between those events and those in the other parameters involved with sleep apnea. If there are substantial numbers of correlations in time, all the respiratory events in the second rank may also be added to those of the first rank by the system user to form the group of most severe significant respiratory events (a "tier" of most severe significant respiratory events) by superimposing another set of criteria over those in the most stringent criteria default setting. Or, alternatively, just those significant respiratory events in the second rank which have correlations in time with one or more other parameters involved in the determination of sleep apnea could be added to those in the more severe rank to form the group of most sever respiratory events (again forming a "tier" of most severe significant respiratory events). Again, system 11 can alternatively itself be set to review correlates and include some fraction or all of them in the most severe group of significant events.

The arousals parameter is in a similar situation with respect to the other parameters involved in insomnia determinations as is the just described respiratory parameter with respect to other sleep apnea parameters. The ranks of less severe significant events for that parameter may be reviewed for time correlations with the other parameters involved in determining occurrences of insomnia to determine whether events in such less severe ranks, which too were excluded from the most severe rank by the default setting threshold and time duration criteria (or by the last choice of superimposed criteria), should not also be added at least in part to the most severe rank of significant events because of the time correlations found to thereby provide a more complete summary of the sleep of subject 10. Here too, system 11 can alternatively itself be set to review correlates and include some fraction or all of them in the most severe group of significant events.

Thus, as shown in FIG. 2I, the user of system 11 is provided with the option of reviewing a display showing the fractions of those significant events occurring in each of the columns of parameters involved in the determination of occurrences of sleep apnea, other than the respiratory parameter, that are correlated with the significant events included in the entire respiratory column, or in just one or more of selected ranks of the respiratory column, through occurring sufficiently close in time to these respiratory significant events. The decision to exercise this option is directly taken in the leftmost decision diamonds in that figure, and can also be invoked from the display of digitized parameter signals in the topmost decision diamond in that figure as indicated above. If chosen, ultimately the display block to the right of that leftmost decision diamond in that figure is reached to implement the providing of a display with that information. A screen with an example of that information in such a display is shown in FIG. 5 with the same number of rows of bar graphs as is shown in the full parameter complement screen of FIG. 4 but with only enough columns for the parameters involved in sleep apnea determination since these are the only correlations that have been found important for that disorder.

Figure 5:
FIG. 5 shows a display used with the system of FIG. 1.

The bar graphs entries in respiratory parameter column in the FIG. 5 screen appear just as they did in the corresponding column of the screen of FIG. 4. However, the remaining parameter columns in the screen of FIG. 5 have the bars therein from the row bar graphs with the same total height that they had in the corresponding parameter columns in the screen of FIG. 4 but with each of the bars split into two parts, one with cross hatching and one without. The portion with cross hatching shows the fraction of significant events total represented in that bar which are correlated in time with a respiratory event, the default time requirement to find a correlation in time being that a parameter significant event occurs within 20 seconds of a respiratory significant event to be considered correlated therewith.

Because the system user may wish to see correlations in time between respiratory significant events and those of other parameters involved with sleep apnea based on various different ranks or combinations of ranks of significant events in the respiratory parameter column, the decision diamond under the display block in FIG. 2I determines whether the base selection of ranks of significant events in the respiratory column is acceptable or whether it is to be changed in the adjustment block to the right of that diamond appearing in FIG. 2J. If there is a such a change implemented by that block, a correlation screen like that of FIG. 5 is displayed because of the return path to the display block in FIG. 2I, the display then showing a screen with the changed base of significant events in the respiratory column as selected and the new fractions indicated of significant events for the other parameters correlated in time thereto. If the base is acceptable, the system user can change the correlation time from the default value of 20 seconds if desired, as is indicated in the uppermost decision diamond in FIG. 2K reached from the lowermost decision diamond in FIG. 2I. If that correlation time is desired to be changed, this change is implemented in the adjustment block to the right of that decision diamond appearing in FIG. 2L, and the result of such a change is redisplayed in a screen display like that of FIG. 5 because of the return to the display block of FIG. 2I.

Figure 2K:
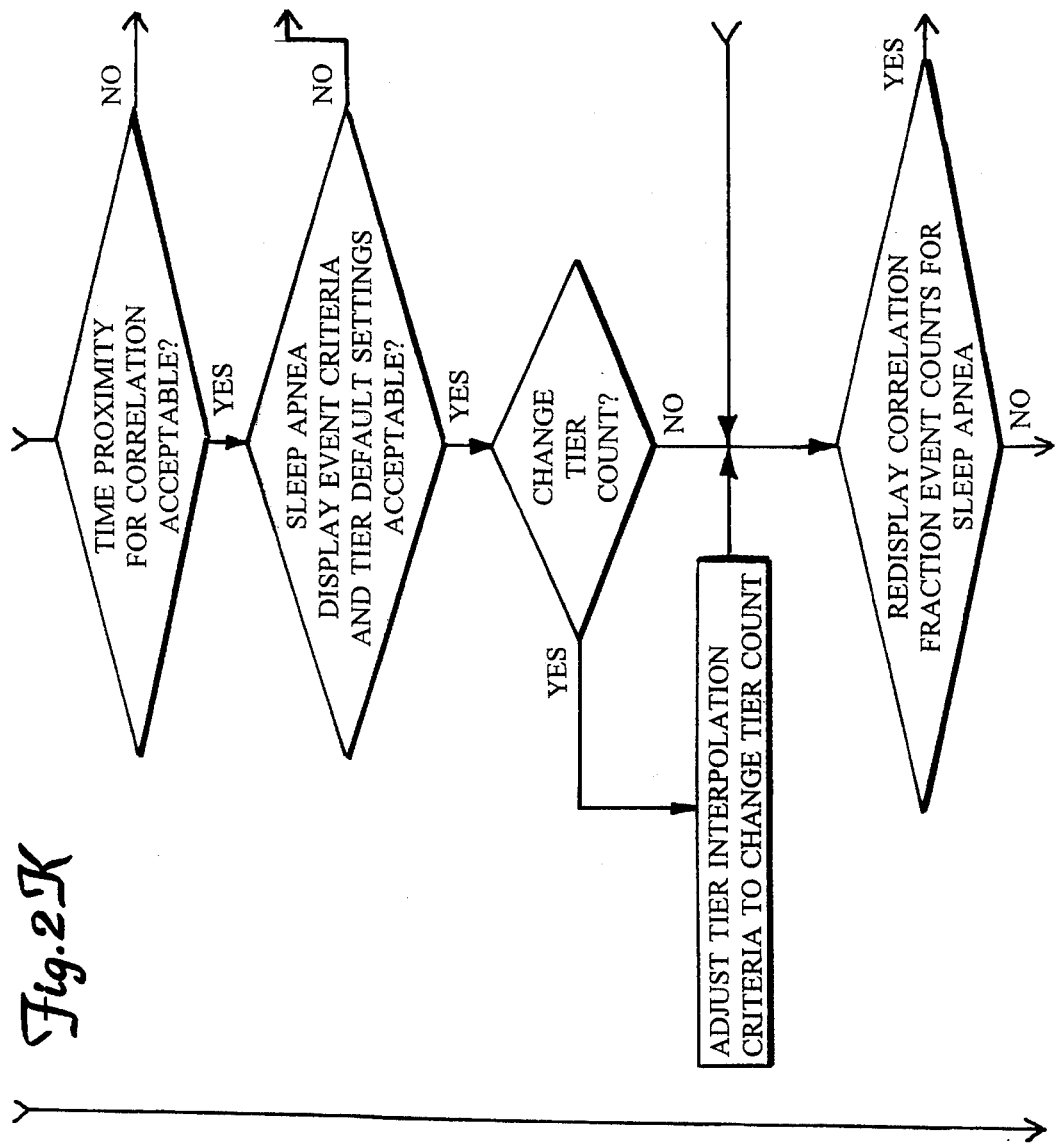
Figure 2L:
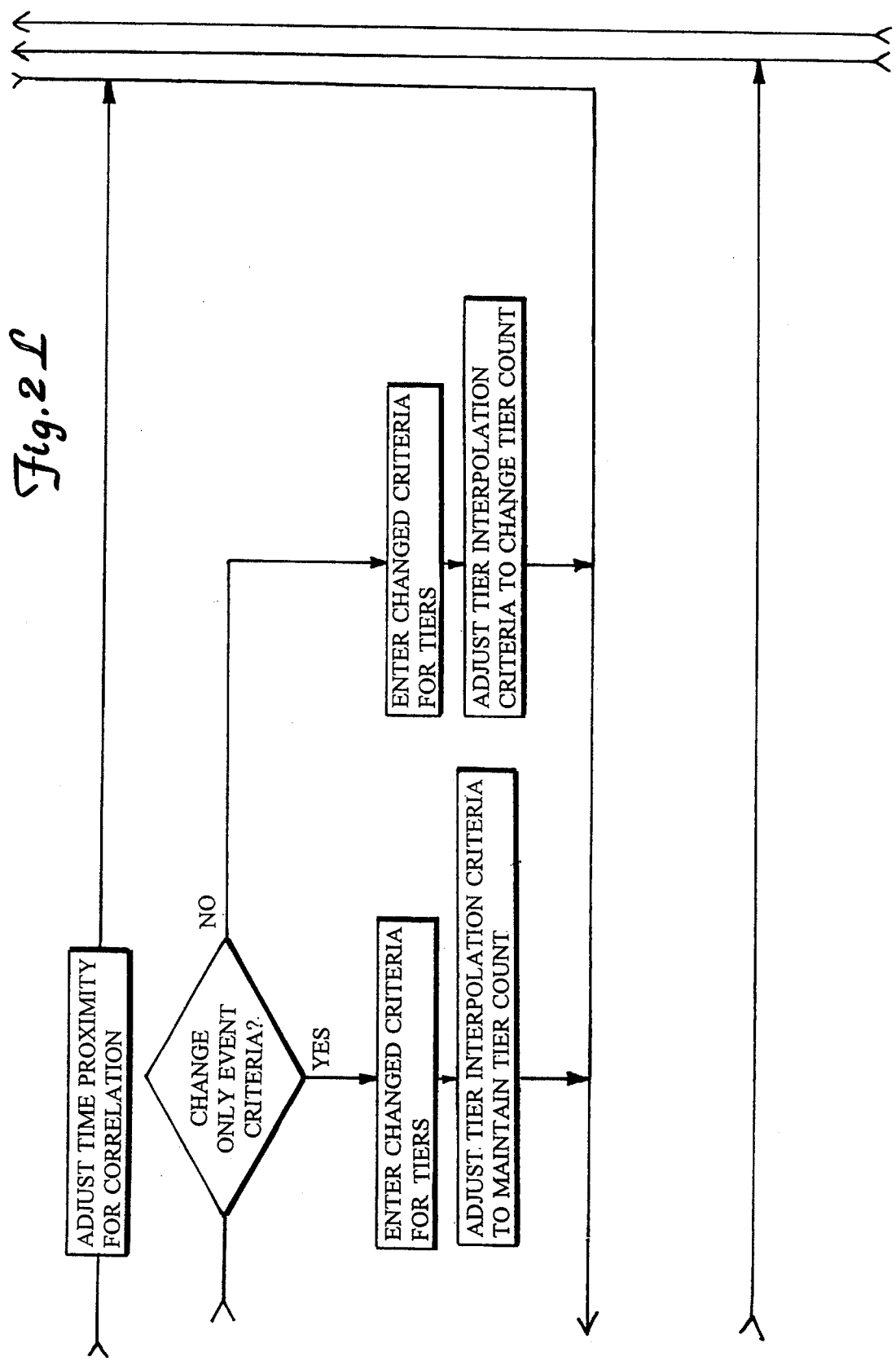
Figure 2M:
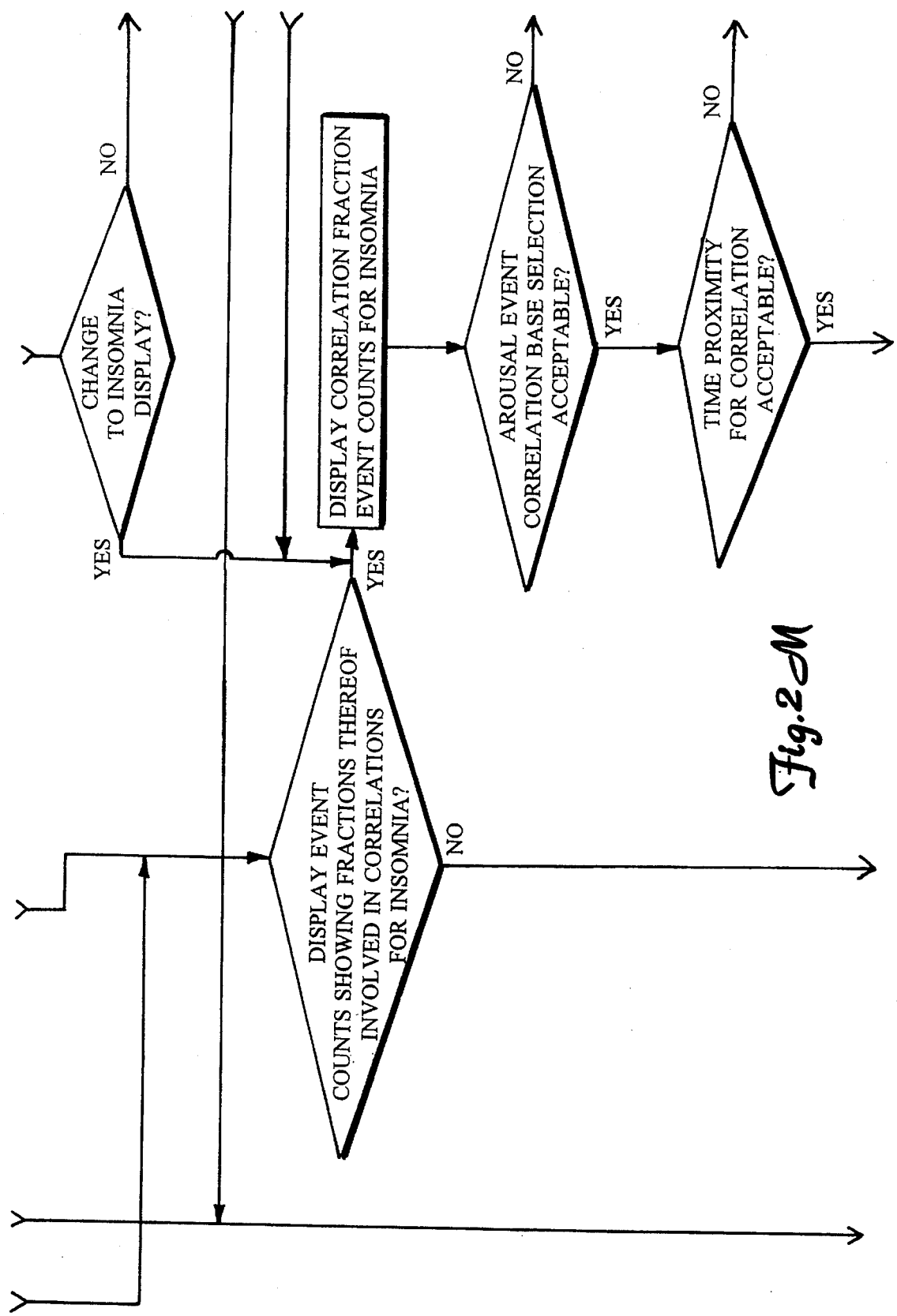
Figure 20:
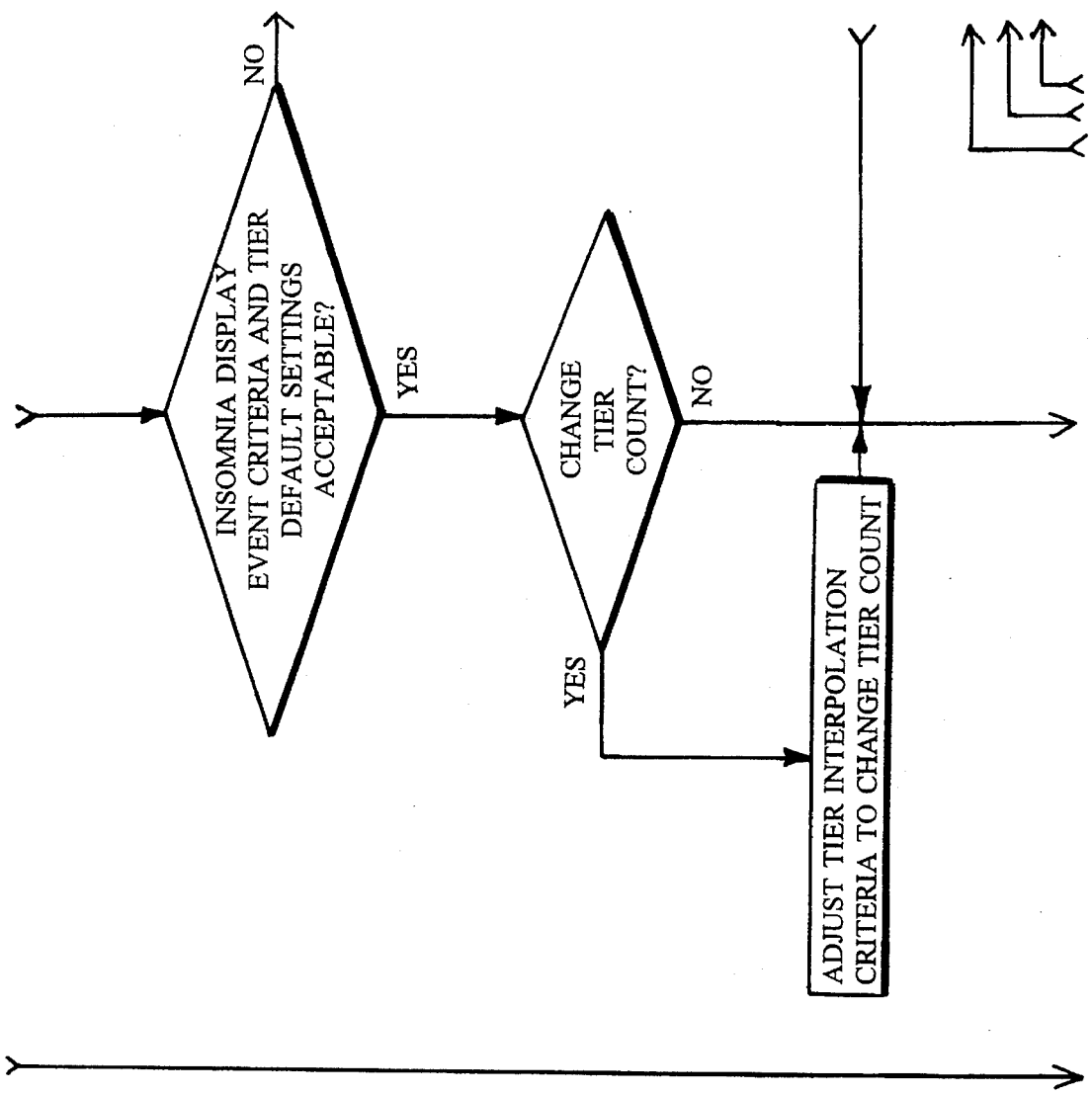

Once these correlation screens for sleep apnea have been adjusted to the satisfaction of the system user for purposes of sleep analysis, the system user is then given the opportunity to change the display event criteria or the default settings if they are no longer acceptable in the next decision diamond down in FIG. 2K. In this situation, most likely, a new set of criteria may be superimposed over the default settings such as adding the next less severe rank thereto or, alternatively, the significant events which are correlated with one or more other parameters may be added to those of the most severe rank. If the constitution of the groups of the most severe significant events remains acceptable, the number of tiers alone may be changed so that more or fewer rows appear in the screen display. These latter kinds of criteria and tier changes are implemented in the remaining decision diamonds and blocks appearing in FIGS. 2K and 2L in just the way they are in matching decision diamonds and blocks of FIGS. 2E and 2F.

The choice of the word "tier" in the flow chart of FIG. 1 can now be seen more clearly. Although there may be a predecessor ranking or grouping of significant events in a parameter signal column, that predecessor accumulation of significant events may be changed in constitution by, for instance, adding other ranks of less severe significant events to that predecessor accumulation to thereby form a new tier of significant events. Alternatively, just correlated ones of less severe significant events may be added to the predecessor rank of most severe events to form a new tier of more severe significant events. Hence, a tier of significant events under a column represents the most recent combination of significant events for a parameter at some severity level of such events.

Figure 6:
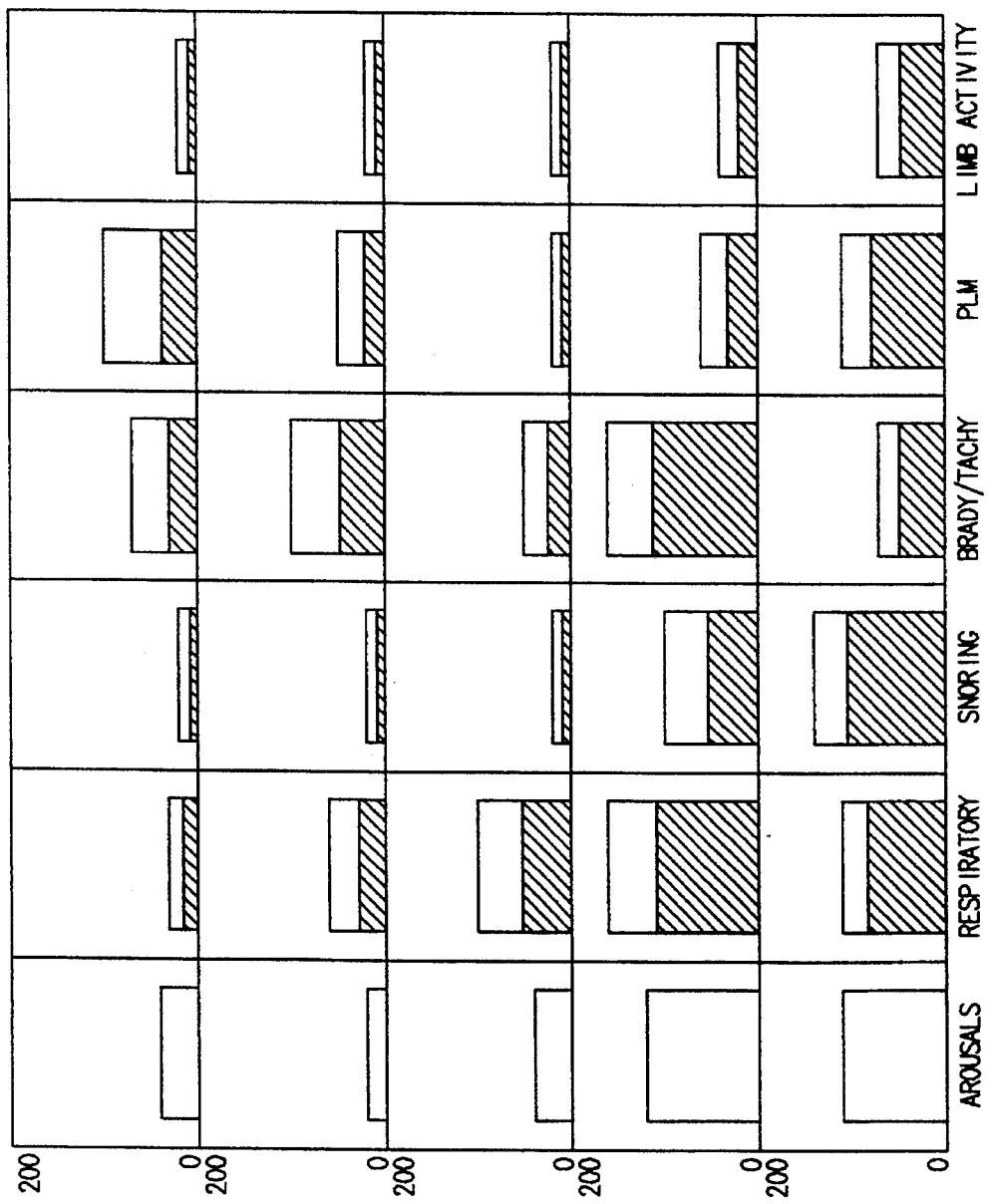
FIG. 6 shows a display used with the system of FIG. 1.

Although the system user will usually wish to redisplay the correlation screen display for sleep apnea as shown in FIG. 5 after making any adjustments, and although sometimes that user may wish to also redisplay the new full parameter complement screen display of FIG. 4, quite often the system user will wish to review the time correlations between arousals and other signal parameters involved in insomnia before actually changing the groupings of most severe events in the lowest row of the screen in FIG. 4. This option is provided either indirectly through the uppermost diamond in FIG. 2M, in transitioning from the sleep apnea correlation display, or directly through the leftmost decision diamond in FIG. 2M if the sleep apnea correlation display was not previously presented on the display monitor of module 17. The display of the insomnia correlation screen is implemented in the display block to the right or below these last two decision diamonds, and leads to a correlation screen display for the parameters as shown in FIG. 6 which, through the correlations in time between the primary arousals parameter significant events and the others, are determinative of the sleep disorder insomnia. Here, the bars of the bar graphs under the arousals column appear just as they did in the screen display of FIG. 4. And again, the remaining signal parameter columns have bars which are the same height as those shown in the corresponding signal parameter columns of FIG. 4 but with cross hatching to show the fraction of significant events in each which correlate in time with the arousals events.

Figure 2Q:
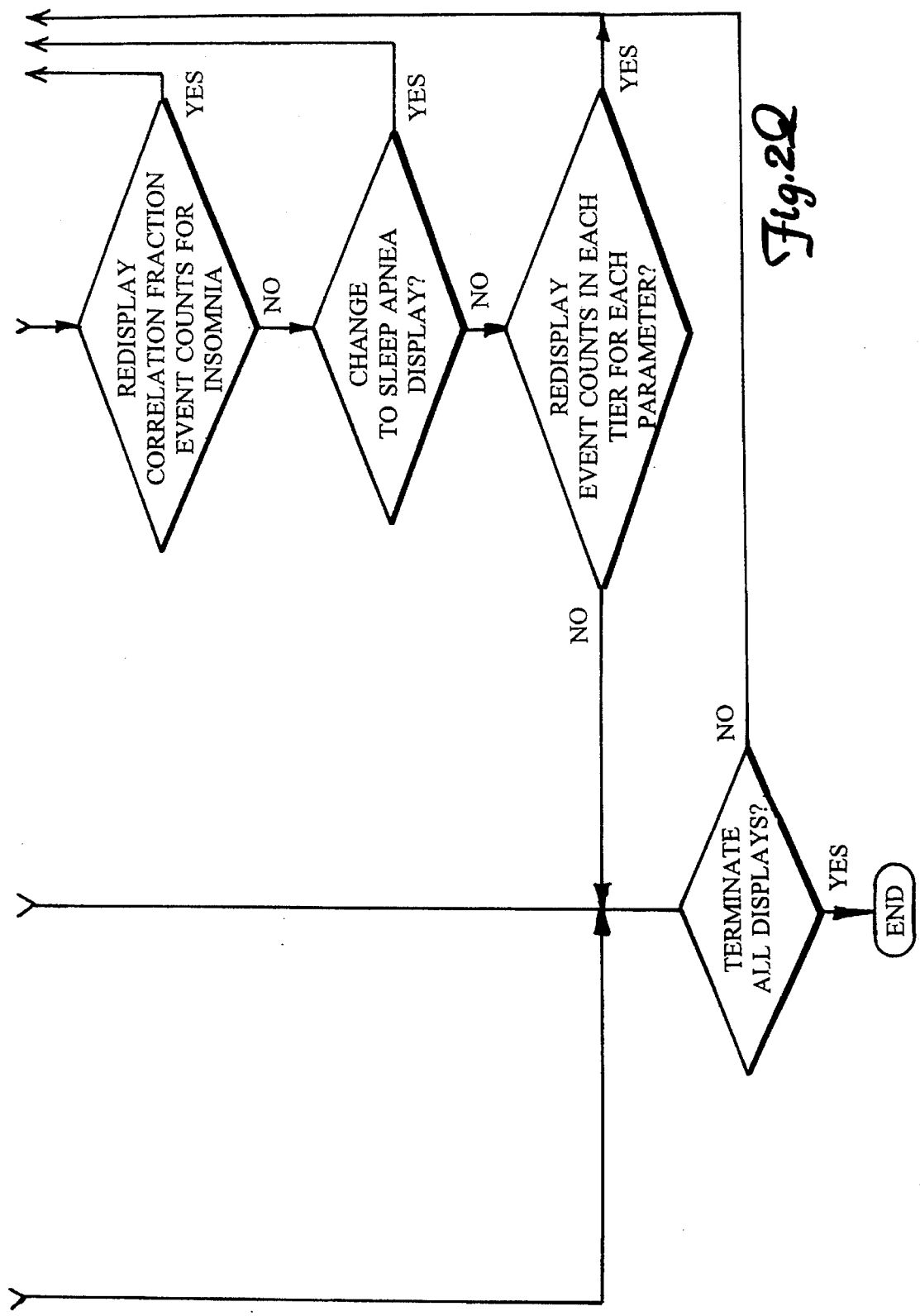
Figure 2R:
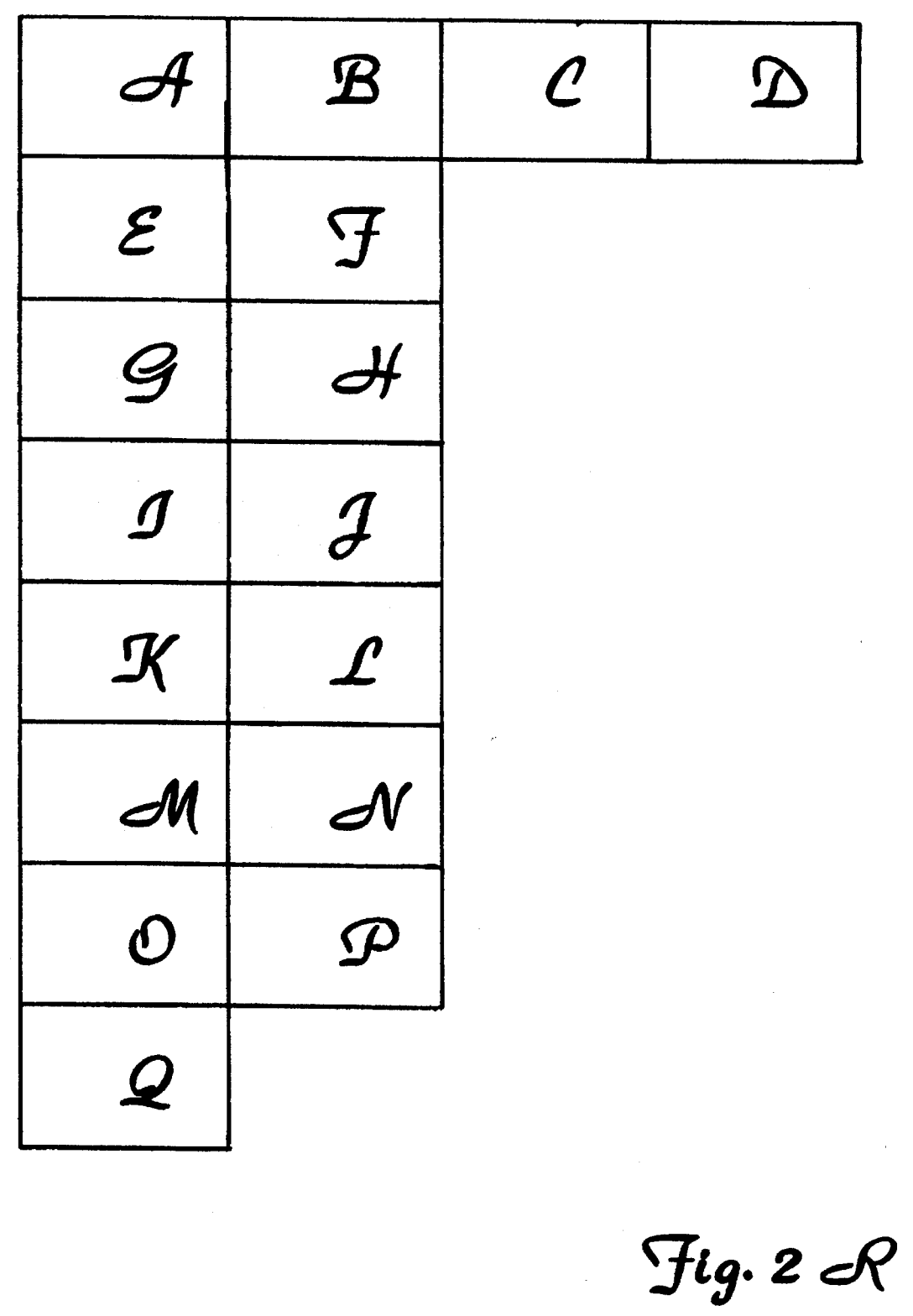

All of the same options for changes in primary parameter significant events bases, correlation time, criteria and number of tiers are available under the insomnia correlation screen display as they were under the sleep apnea correlation screen display, and so the corresponding decision diamonds and adjustment blocks appear under that display block in FIGS. 2M, 2N, 2O and 2P as appeared under the sleep apnea display block shown in FIGS. 2I, 2J, 2K and 2L. As a result, the same implementation steps are followed in making changes for either screen. As can be seen in FIG. 2Q, the insomnia correlation screen display can be redisplayed after any adjustments are made, or the system user can go back to the sleep apnea display screen in connection with any adjustments being made if desired.

Further, the information assembled for the display of screens like those shown in FIGS. 5 and 6 can be used to provide further screens (not shown) noting the apnea, hypopneas and arousals (substantiated by more than EEG and chin EMG signal events) found from the correlations in time present. In connection with the sleep apnea parameters, as indicated above, apneas are on an absolute scale of respiratory events without regard to time correlations with other parameters in that they represent essentially a cessation of breathing for a minimum period of time. They will be noted upon every such occurrence (the respiratory signal having a magnitude that drops to less than 15% full scale for 10 seconds or more). Hypopneas, on the other hand, will be noted for respiratory events that are not apneas but meet the respiratory significant event most stringent criteria after the most severe events tier is determined and such events are correlated in time with any of a 2% desaturation, a 4 beat/min heart rate change, or an arousal, with the option of noting them only if all three of these time correlates are present. Correlation in time here again means the events being correlated occurring within 20 seconds of one another.

Possible hypopneas will be noted for respiratory events meeting the less stringent criteria therefor after tier determination correlated with any of a 2% desaturation, a 6 beat/min heart rate change, or an arousal, again with the possibility of requiring the occurrence of all three of these correlates.

Substantiated arousals will be noted for arousal events meeting the most stringent criteria therefor after tier determination which are correlated in time with any of a respiratory event, a snoring event, a periodic limb movement, another limb activity movement of a magnitude of 10% of full scale or more, or a 4 beat/min heart rate change. Possible substantiated arousals will be noted for arousal events meeting the less stringent criteria therefor after tier determination which are correlated in time with any of a respiratory event, a snoring event, a periodic limb movement, another limb activity movement of a magnitude of 15% of full scale or more, or a 6 beat/min heart rate change.

Figure 7:
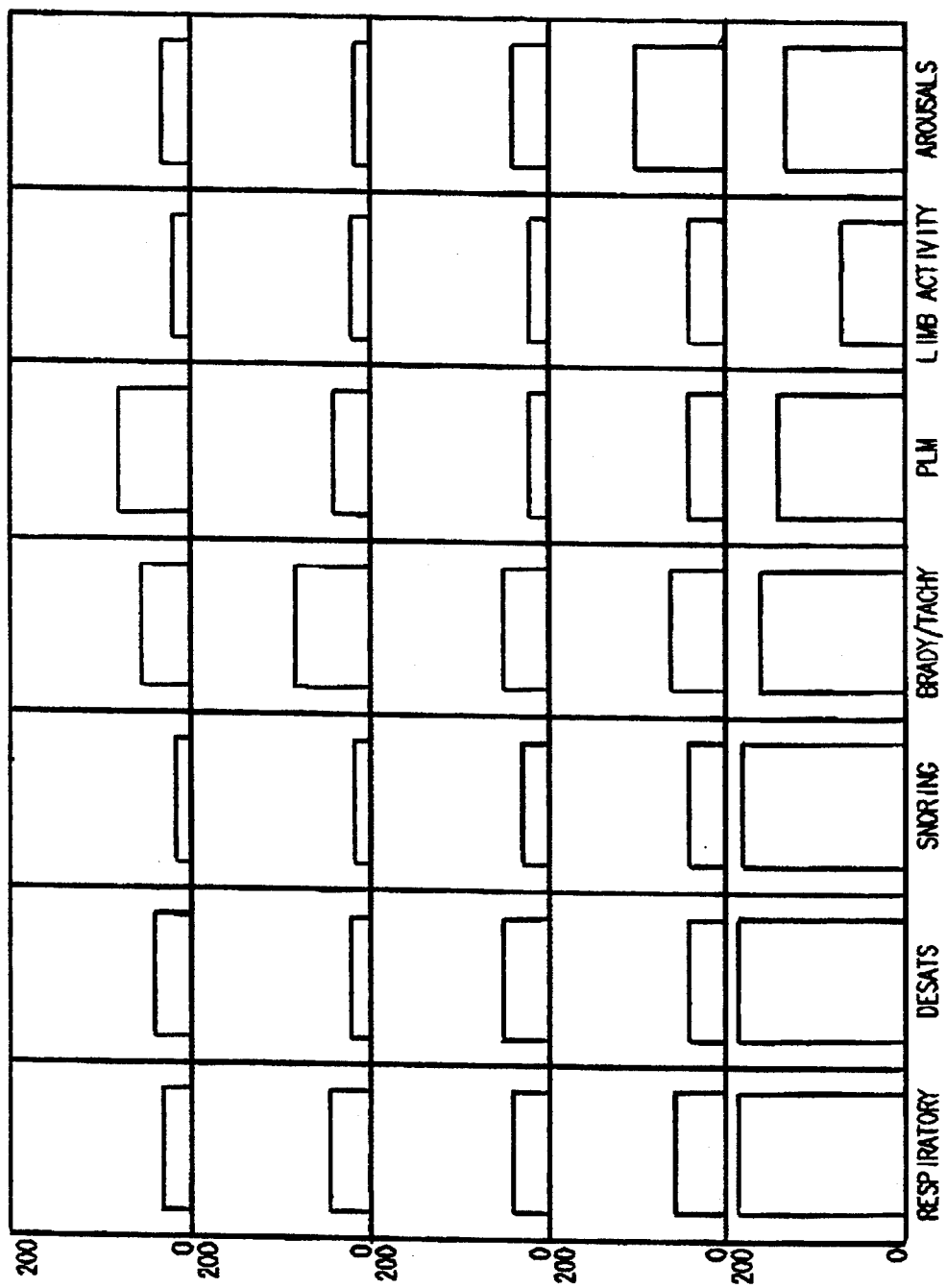
FIG. 7 shows a display used with the system of FIG. 1.

Finally, after all adjustments in criteria for ranks, or for the designated additions of correlated significant events to most severe tier, have been made, the complete results reflected in the new tiers of significant events for all of the parameters can be redisplayed as implemented in the display block at the top of FIG. 2E because of the return to there from either of the correlation display screens. An example of such changed tier results is shown in the screen for the full parameter complement as shown in FIG. 7 which is appropriate in view of the screens shown in FIGS. 4, 5 and 6. Although the format of the screen on the display in module 17 for the screen of FIG. 7 is identical to that for the screen shown in FIG. 4, the bar graphs for each of the rows can be seen to have changed in the screen of FIG. 7 with the lowest row bar graph containing the most severe significant events having bars therein which have increased substantially in height. Such increases indicate more significant events have been added thereto as compared with the initial rank of most severe significant events appearing on the screen in the display shown in FIG. 4. Thus, this most severe tier of significant events is ready to be reported as summarizing the sleep of subject 10 during the analysis sleep episode with the count values therein fully reviewed with respect to the remaining significant events appearing in the other tiers so as to be sure that nearly all those clinically relevant appear in this most severe significant events tier.

Although the present invention has been described with reference to preferred embodiments, workers skilled in the art will recognize that changes may be made in form and detail without departing from the spirit and scope of the invention.

What is claimed is:

1. A method for analyzing a sleep episode of a subject based on measured values of a plurality of parameters characterizing physiological activity of that subject during such an episode, said method comprising:

acquiring from said subject a plurality of parameter signals each representing values occurring during at least parts of said episode of a corresponding one of said plurality of parameters;

classifying portions of each of said plurality of parameter signals as significant events for that said parameter corresponding thereto based on selected signal criteria including classifying such significant events of a first parameter signal, corresponding to a first parameter, into a plurality of ranks having among them an initial rank of those first parameter significant events corresponding to portions of said first parameter signal having values beyond an initial first parameter threshold; and segregating from said first parameter significant events those (i) which (a) are said initial rank first parameter significant events, and those which (b) are in one of said plurality of ranks other than said initial rank but occur within a selected time of any of a first selection of significant events of another of said plurality of parameters to form a first tier of said first parameter significant events in a plurality of tiers of said first parameter significant events, and those (ii) which are in said plurality of ranks of said first parameter significant events without being in said first tier of first parameter significant events to form at least a second tier in said plurality of tiers of said first parameter significant events.

2. The method of claim 1 further comprising counting said first parameter significant events in said plurality of tiers to provide total counts thereof, and providing a visual display in which representations of said total counts of said first and second tiers of said first parameter significant events are provided.

3. The method of claim 2 wherein said first tier of said first parameter significant events includes those said first parameter significant parameter events which are in one of said plurality of ranks other than said initial rank but occur within a selected time of one of a first selection of significant parameter events of a second parameter; and further comprising counting said selected second parameter significant parameter events to provide a total count thereof, and providing a representation of said total count of said selected second parameter significant parameter events in said visual display.

4. The method of claim 3 further comprising counting said first parameter significant events in said plurality of tiers to provide total counts thereof, and displaying representations of said total counts of said first and second tiers of said first parameter significant events on said visual display.

5. The method of claim 1 wherein said first tier of said first parameter significant events includes those said first parameter significant events which are in one of said plurality of ranks other than said initial rank but occur within a selected time of any of a first selection of significant events of a second parameter, and wherein said segregating from said first parameter significant events further comprises segregating those which are in one of said plurality of ranks other than said initial rank but occur within a selected time of any of selected said significant events of a third parameter.

6. The method of claim 5 further comprising counting said selected second and third parameter significant events to provide total counts thereof, and providing a representation of said total counts of said selected second and third parameter significant events in a visual display.

7. The method of claim 6 further comprising indicating on said visual display those fractions of said second and third count totals which occur within said selected times of any of said first parameter significant events.

8. The method of claim 7 further comprising counting said first parameter significant events in said plurality of tiers to provide total counts thereof, and displaying representations of said total counts of said first and second tiers of said first parameter significant events on said visual display.

9. The method of claim 6 further comprising counting said first parameter significant events in said plurality of tiers to provide total counts thereof, and displaying representations of said total counts of said first and second tiers of said first parameter significant events on said visual display.

10. The method of claim 5 wherein said segregating from said first parameter significant events includes segregating, from among those said first parameter significant events that occur within selected times of any of said selected second and third parameter significant events, just those occurring within a second parameter selected time of a said second parameter significant event and within a third parameter selected time of a said third parameter significant event.

11. The method of claim 1 wherein said classifying of said significant events of a first parameter signal corresponding to a first parameter into a plurality of ranks further includes having among said plurality of ranks a baseline rank of those first parameter significant events corresponding to portions of said first parameter signal having values beyond a baseline first parameter threshold but within said initial first parameter threshold.

12. The method of claim 11 wherein said classifying of said significant events of a first parameter signal corresponding to a first parameter into a plurality of ranks further includes having those of said plurality of ranks of first parameter significant events other than said initial and baseline ranks contain first parameter significant events corresponding to portions of said first parameter signal having values beyond a corresponding one of an ordered set of interpolated first parameter thresholds ordered by magnitude and within that next in order one of said interpolative first parameter thresholds, said set of interpolative first parameter thresholds all being beyond said baseline first parameter threshold in magnitude and within said initial first parameter threshold in magnitude.

13. The method of claim 1 wherein said segregating from said first parameter significant events includes forming said first tier of said first parameter significant events with all of said first parameter significant events which are in one of said plurality of ranks other than said initial rank.

14. The method of claim 1 further comprising changing said first tier of said first parameter significant events to form a revised first tier of said first parameter significant events by selecting one of a further set of steps comprising an addition thereto of other selected said first parameter significant events and an exclusion therefrom of selected said first parameter significant events previously included therein.

15. The method of claim 1 wherein said first tier of said first parameter significant events includes those said first parameter significant events which are in one of said plurality of ranks other than said initial rank but occur within a selected time of any of a first selection of significant parameter events of a second parameter; and further comprising counting said second parameter significant events to provide a total count thereof and providing a visual display in which a representation of said total count of said second parameter significant events is provided so as to indicate that fraction thereof which occurs within said selected time of any of said first parameter significant events.

16. The method of claim 15 further comprising counting said first parameter significant events in said plurality of tiers to provide total counts thereof, and displaying representations of said total counts of said first and second tiers of said first parameter significant events on said visual display.

17. The method of claim 1 wherein said acquiring of a plurality of parameter signals is accomplished through sensing said parameters with corresponding sensors that are positioned on said subject so as to provide a corresponding sensor signal.

18. The method of claim 17 wherein said sensor signals are analog signals, and further comprises converting said analog signals to digital signals.

19. A sleep analysis system for analyzing a sleep episode of a subject based on measured values of a plurality of parameters characterizing that subject during such an episode, said system comprising:

a signal acquiring means for acquiring a plurality of parameter signals each representing values of a corresponding one of said plurality of parameters occurring during at least parts of said episode;

an analog-to-digital converter means coupled to said signal acquiring means for providing corresponding sequences of digitized samples amplitude values of said parameter signals;

a display and input means for providing displays of representations of said parameter signals provided at inputs thereof, and capable of providing selected values at outputs thereof;

a signal processing means coupled to said analog-to-digital converter means and to said inputs and outputs of said display and input means, and capable of classifying portions of each of said plurality of parameter signals as significant events for that said parameter corresponding thereto based on selected signal criteria including classifying such significant events of a first parameter signal, corresponding to a first parameter, into a plurality of ranks having among them an initial rank of those first parameter significant events corresponding to portions of said first parameter signal having values beyond an initial first parameter threshold, and of segregating from said first parameter significant events those (i) which (a) are said initial rank first parameter significant events, and those which (b) are in one of said plurality of ranks other than said initial rank but occur within a selected time of any of a first selection of significant events of at least one other of said plurality of parameters to form a first tier of said first parameter significant events in a plurality of tiers of said first parameter significant events, and those (ii) which are in said plurality of ranks of said first parameter significant events without being in said first tier of first parameter significant events to form at least a second tier in said plurality of tiers of said first parameter significant events.

20. The apparatus of claim 19 wherein said display and input means further comprises a visual display, and wherein said signal processing means is capable of counting said first parameter significant events in said plurality of tiers to provide total counts thereof, and of displaying representations of said total counts of said first and second tiers of said first parameter significant events on said visual display.

21. The apparatus of claim 20 wherein said first tier of said first parameter significant events includes those said first parameter significant events which are in one of said plurality ranks other than said initial rank but occur within a selected time of any of a first selection of significant parameter events of a second parameter; and wherein said signal processing means is further capable of counting said second parameter significant events to provide a total count thereof and providing a representation of said total count of said second parameter events in said visual display.

22. The apparatus of claim 19 wherein said first tier of first parameter significant events includes those said first parameter significant events which are in one of said plurality of ranks other than said initial rank but occur within a selected time of any of a first selection of significant events of a second parameter, and wherein said signal processing means is further capable of segregating from said first parameter significant events those which are in one of said plurality of ranks other than said initial rank but that occur within a selected time of any of selected said significant events of a third parameter.

23. The apparatus of claim 22 further wherein said signal processing means is further capable of counting said selected second and third parameter significant events to provide total counts thereof and providing a representation of said total counts of said selected second and third parameter significant events in said visual display.

24. The apparatus of claim 23 wherein there is indicated on said visual display those fractions of said second and third count totals which occur within said selected times of one of said first parameter significant events.

25. The apparatus of claim 22 wherein said signal processing means is further capable of segregating, from among those said first parameter significant events that occur within selected times of any of said selected second and third parameter significant events, just those occurring within a second parameter selected time of a said second parameter significant event and within a third parameter selected time of a said third parameter significant event.

26. The apparatus of claim 19 wherein said plurality of ranks includes a baseline rank of those first parameter significant events corresponding to portions of said first parameter signal having values beyond a baseline first parameter threshold but within said initial first parameter threshold.

27. The apparatus of claim 26 wherein those of said plurality of ranks of first parameter significant events other than said initial and baseline ranks contain first parameter significant events corresponding to portions of said first parameter signal having values beyond a corresponding one of an ordered set of interpolated first parameter thresholds ordered by magnitude and within that next in order one of said interpolative first parameter thresholds, said set of interpolative first parameter thresholds all being beyond said baseline first parameter threshold in magnitude and within said initial first parameter threshold in magnitude.

28. The apparatus of claim 19 wherein said signal processing means is further capable of forming said first tier of said first parameter significant events with all of said first parameter significant events which are in one of said plurality of ranks other than said initial rank.

29. The apparatus of claim 19 wherein said signal processing means is further capable of changing said first tier of said first parameter significant events to form a revised first tier of said first parameter significant events by selecting one of a further set of steps comprising in addition thereto of other selected said first parameter significant events and an exclusion therefrom of selected said first parameter significant events previously included therein.

30. The apparatus of claim 19 wherein said first tier of said first parameter significant events includes those said first parameter significant events which are in one of said plurality ranks other than said initial rank but occur within a selected time of any of a first selection of significant parameter events of a second parameter; and wherein said signal processing means is further capable of counting said second parameter significant events to provide a total count thereof and providing a representation of said total count of said second parameter events in said visual display so as to indicate that fraction thereof which occurs within said selected time of any of said first parameter significant events.

* * * * *

UNITED STATES PATENT AND TRADEMARK OFFICE
CERTIFICATE OF CORRECTION

PATENT NO. : 5,520,176
DATED : May 28, 1996
INVENTOR(S) : DANIEL E. COHEN

It is certified that error appears in the above-indentified patent and that said Letters Patent is hereby corrected as shown below:

Col. 9, line 66, after "measurement", delete "alter", insert --after--

Signed and Sealed this

Twenty-seventh Day of August, 1996

Attest:

BRUCE LEHMAN

*Attesting Officer*    *Commissioner of Patents and Trademarks*